United States Patent
Jascob et al.

(10) Patent No.: US 9,675,424 B2
(45) Date of Patent: Jun. 13, 2017

(54) METHOD FOR CALIBRATING A NAVIGATION SYSTEM

(75) Inventors: Bradley Jascob, Broomfield, CO (US); David Simon, Boulder, CO (US); Paul Kessman, Broomfield, CO (US); Aaron Smith, Denver, CO (US)

(73) Assignee: SURGICAL NAVIGATION TECHNOLOGIES, INC., Louisville, CO (US)

(*) Notice: Subject to any disclaimer, the term of this patent is extended or adjusted under 35 U.S.C. 154(b) by 2410 days.

(21) Appl. No.: 12/507,722

(22) Filed: Jul. 22, 2009

(65) Prior Publication Data

US 2009/0287443 A1 Nov. 19, 2009

Related U.S. Application Data

(60) Division of application No. 10/649,214, filed on Aug. 26, 2003, now abandoned, which is a continuation of
(Continued)

(51) Int. Cl.
*A61B 19/00* (2006.01)
*A61B 90/00* (2016.01)
(Continued)

(52) U.S. Cl.
CPC .............. *A61B 90/36* (2016.02); *A61B 34/20* (2016.02); *A61B 2017/00725* (2013.01);
(Continued)

(58) Field of Classification Search
CPC ...... G01R 29/08; G01R 31/2822; G01R 3/00; G01R 1/06705; A61N 1/40; A61N 2/006;
(Continued)

(56) References Cited

U.S. PATENT DOCUMENTS

| 1,576,781 A | 3/1926 | Phillips |
| 1,735,726 A | 11/1929 | Bornhardt |

(Continued)

FOREIGN PATENT DOCUMENTS

| CA | 964149 | 3/1975 |
| DE | 3042343 | 6/1982 |

(Continued)

OTHER PUBLICATIONS

"Prestige Cervical Disc System Surgical Technique", 12 pgs.
(Continued)

*Primary Examiner* — Son Le
*Assistant Examiner* — Alesa Allgood
(74) *Attorney, Agent, or Firm* — Harness Dickey

(57) ABSTRACT

A method and apparatus for electromagnetic navigation of a surgical probe near a metal object. The electromagnetic navigation system includes a transmitter coil array and a shield. The transmitter coil array has a plurality of transmitter coils and is operable to generate the electromagnetic field to navigate the probe. The shield is positioned adjacent the metal object and is operable to shield the metal object from the electromagnetic field generated by the transmitter coil array, such that the shield substantially reduces distortion of the electromagnetic field by the metal object.

44 Claims, 10 Drawing Sheets

Related U.S. Application Data application No. 09/873,604, filed on Jun. 4, 2001, now Pat. No. 6,636,757.

(51) Int. Cl.
  *A61B 17/00* (2006.01)
  *A61B 34/20* (2016.01)

(52) U.S. Cl.
  CPC .............. *A61B 2019/4081* (2013.01); *A61B 2034/2051* (2016.02); *A61B 2034/2072* (2016.02); *A61B 2090/376* (2016.02)

(58) Field of Classification Search
  CPC .... A61N 1/0456; A61N 2/02; A61N 1/36014; A61N 2/008; A61N 1/36021; A61N 1/36053; A61N 1/36075; A61N 1/0517; A61N 1/36007; A61N 1/36025; A61N 1/36114; A61N 1/3601; A61N 1/056; A61B 5/06; A61B 18/1492; A61B 2019/5251; A61B 19/5244; A61B 5/065; A61B 5/6885; A61B 5/062; A61B 2018/00577; A61B 5/6852; A61B 2017/00725; A61B 5/1495; A61M 25/0127; A61M 25/00
  USPC .................. 324/202, 207.23, 207.13, 207.17; 600/424; 702/150
  See application file for complete search history.

(56) References Cited

U.S. PATENT DOCUMENTS

| | | |
|---|---|---|
| 2,407,845 A | 9/1946 | Nemeyer |
| 2,650,588 A | 9/1953 | Drew |
| 2,697,433 A | 12/1954 | Sehnder |
| 3,016,899 A | 1/1962 | Stenvall |
| 3,017,887 A | 1/1962 | Heyer |
| 3,061,936 A | 11/1962 | Dobbeleer |
| 3,073,310 A | 1/1963 | Mocarski |
| 3,109,588 A | 11/1963 | Polhemus et al. |
| 3,294,083 A | 12/1966 | Alderson |
| 3,367,326 A | 2/1968 | Frazier |
| 3,439,256 A | 4/1969 | Kahne |
| 3,526,798 A | 9/1970 | Sandstorm |
| 3,577,160 A | 5/1971 | White |
| 3,614,950 A | 10/1971 | Rabey |
| 3,644,825 A | 2/1972 | Davis, Jr. et al. |
| 3,674,014 A | 7/1972 | Tillander |
| 3,702,935 A | 11/1972 | Carey et al. |
| 3,704,707 A | 12/1972 | Halloran |
| 3,821,469 A | 6/1974 | Whetstone et al. |
| 3,868,565 A | 2/1975 | Kuipers |
| 3,941,127 A | 3/1976 | Froning |
| 3,983,474 A | 9/1976 | Kuipers |
| 4,017,858 A | 4/1977 | Kuipers |
| 4,037,592 A | 7/1977 | Kronner |
| 4,052,620 A | 10/1977 | Brunnett |
| 4,054,881 A | 10/1977 | Raab |
| 4,117,337 A | 9/1978 | Staats |
| 4,137,361 A | 1/1979 | Deffeyes et al. |
| 4,173,228 A | 11/1979 | Van Steenwyk et al. |
| 4,182,312 A | 1/1980 | Mushabac |
| 4,202,349 A | 5/1980 | Jones |
| 4,228,799 A | 10/1980 | Anichkov et al. |
| 4,256,112 A | 3/1981 | Kopf et al. |
| 4,262,306 A | 4/1981 | Renner |
| 4,287,809 A | 9/1981 | Egli et al. |
| 4,298,874 A | 11/1981 | Kuipers |
| 4,314,251 A | 2/1982 | Raab |
| 4,317,078 A | 2/1982 | Weed et al. |
| 4,319,136 A | 3/1982 | Jinkins |
| 4,328,548 A | 5/1982 | Crow et al. |
| 4,328,813 A | 5/1982 | Ray |
| 4,339,953 A | 7/1982 | Iwasaki |
| 4,341,220 A | 7/1982 | Perry |
| 4,346,384 A | 8/1982 | Raab |
| 4,358,856 A | 11/1982 | Stivender et al. |
| 4,368,536 A | 1/1983 | Pfeiler |
| 4,396,885 A | 8/1983 | Constant |
| 4,396,945 A | 8/1983 | DiMatteo et al. |
| 4,403,321 A | 9/1983 | Kruger |
| 4,418,422 A | 11/1983 | Richter et al. |
| 4,419,012 A | 12/1983 | Stephenson et al. |
| 4,422,041 A | 12/1983 | Lienau |
| 4,431,005 A | 2/1984 | McCormick |
| 4,485,815 A | 12/1984 | Amplatz et al. |
| 4,506,676 A | 3/1985 | Duska |
| 4,543,959 A | 10/1985 | Sepponen |
| 4,548,208 A | 10/1985 | Niemi |
| 4,571,834 A | 2/1986 | Fraser et al. |
| 4,572,198 A | 2/1986 | Codrington |
| 4,583,538 A | 4/1986 | Onik et al. |
| 4,584,577 A | 4/1986 | Temple |
| 4,608,977 A | 9/1986 | Brown |
| 4,613,866 A | 9/1986 | Blood |
| 4,617,925 A | 10/1986 | Laitinen |
| 4,618,978 A | 10/1986 | Cosman |
| 4,621,628 A | 11/1986 | Brudermann |
| 4,625,718 A | 12/1986 | Olerud et al. |
| 4,638,798 A | 1/1987 | Shelden et al. |
| 4,642,786 A | 2/1987 | Hansen |
| 4,645,343 A | 2/1987 | Stockdale et al. |
| 4,649,504 A | 3/1987 | Krouglicof et al. |
| 4,651,732 A | 3/1987 | Frederick |
| 4,653,509 A | 3/1987 | Oloff et al. |
| 4,659,971 A | 4/1987 | Suzuki et al. |
| 4,660,970 A | 4/1987 | Ferrano |
| 4,673,352 A | 6/1987 | Hansen |
| 4,688,037 A | 8/1987 | Krieg |
| 4,701,049 A | 10/1987 | Beckman et al. |
| 4,705,395 A | 11/1987 | Hageniers |
| 4,705,401 A | 11/1987 | Addleman et al. |
| 4,706,665 A | 11/1987 | Gouda |
| 4,709,156 A | 11/1987 | Murphy et al. |
| 4,710,708 A | 12/1987 | Rorden et al. |
| 4,719,419 A | 1/1988 | Dawley |
| 4,722,056 A | 1/1988 | Roberts et al. |
| 4,722,336 A | 2/1988 | Kim et al. |
| 4,723,544 A | 2/1988 | Moore et al. |
| 4,727,565 A | 2/1988 | Ericson |
| RE32,619 E | 3/1988 | Damadian |
| 4,733,969 A | 3/1988 | Case et al. |
| 4,737,032 A | 4/1988 | Addleman et al. |
| 4,737,794 A | 4/1988 | Jones |
| 4,737,921 A | 4/1988 | Goldwasser et al. |
| 4,742,356 A | 5/1988 | Kuipers |
| 4,742,815 A | 5/1988 | Ninan et al. |
| 4,743,770 A | 5/1988 | Lee |
| 4,743,771 A | 5/1988 | Sacks et al. |
| 4,745,290 A | 5/1988 | Frankel et al. |
| 4,750,487 A | 6/1988 | Zanetti |
| 4,753,528 A | 6/1988 | Hines et al. |
| 4,761,072 A | 8/1988 | Pryor |
| 4,764,016 A | 8/1988 | Johansson |
| 4,771,787 A | 9/1988 | Wurster et al. |
| 4,779,212 A | 10/1988 | Levy |
| 4,782,239 A | 11/1988 | Hirose et al. |
| 4,788,481 A | 11/1988 | Niwa |
| 4,791,934 A | 12/1988 | Brunnett |
| 4,793,355 A | 12/1988 | Crum et al. |
| 4,794,262 A | 12/1988 | Sato et al. |
| 4,797,907 A | 1/1989 | Anderton |
| 4,803,976 A | 2/1989 | Frigg et al. |
| 4,804,261 A | 2/1989 | Kirschen |
| 4,805,615 A | 2/1989 | Carol |
| 4,809,694 A | 3/1989 | Ferrara |
| 4,821,200 A | 4/1989 | Oberg |
| 4,821,206 A | 4/1989 | Arora |
| 4,821,731 A | 4/1989 | Martinelli et al. |
| 4,822,163 A | 4/1989 | Schmidt |
| 4,825,091 A | 4/1989 | Breyer et al. |
| 4,829,373 A | 5/1989 | Leberl et al. |
| 4,836,778 A | 6/1989 | Baumrind et al. |

(56) References Cited

U.S. PATENT DOCUMENTS

| | | |
|---|---|---|
| 4,838,265 A | 6/1989 | Cosman et al. |
| 4,841,967 A | 6/1989 | Chang et al. |
| 4,845,771 A | 7/1989 | Wislocki et al. |
| 4,849,692 A | 7/1989 | Blood |
| 4,860,331 A | 8/1989 | Williams et al. |
| 4,862,893 A | 9/1989 | Martinelli |
| 4,869,247 A | 9/1989 | Howard, III et al. |
| 4,875,165 A | 10/1989 | Fencil et al. |
| 4,875,478 A | 10/1989 | Chen |
| 4,884,566 A | 12/1989 | Mountz et al. |
| 4,889,526 A | 12/1989 | Rauscher et al. |
| 4,896,673 A | 1/1990 | Rose et al. |
| 4,905,698 A | 3/1990 | Strohl, Jr. et al. |
| 4,923,459 A | 5/1990 | Nambu |
| 4,931,056 A | 6/1990 | Ghajar et al. |
| 4,945,305 A | 7/1990 | Blood |
| 4,945,914 A | 8/1990 | Allen |
| 4,951,653 A | 8/1990 | Fry et al. |
| 4,955,891 A | 9/1990 | Carol |
| 4,961,422 A | 10/1990 | Marchosky et al. |
| 4,977,655 A | 12/1990 | Martinelli |
| 4,989,608 A | 2/1991 | Ratner |
| 4,991,579 A | 2/1991 | Allen |
| 5,002,058 A | 3/1991 | Martinelli |
| 5,005,592 A | 4/1991 | Cartmell |
| 5,013,317 A | 5/1991 | Cole et al. |
| 5,016,639 A | 5/1991 | Allen |
| 5,017,139 A | 5/1991 | Mushabac |
| 5,027,818 A | 7/1991 | Bova et al. |
| 5,030,196 A | 7/1991 | Inoue |
| 5,030,222 A | 7/1991 | Calandruccio et al. |
| 5,031,203 A | 7/1991 | Trecha |
| 5,042,486 A | 8/1991 | Pfeiler et al. |
| 5,047,036 A | 9/1991 | Koutrouvelis |
| 5,050,608 A | 9/1991 | Watanabe et al. |
| 5,054,492 A | 10/1991 | Scribner et al. |
| 5,057,095 A | 10/1991 | Fabian |
| 5,059,789 A | 10/1991 | Salcudean |
| 5,078,140 A | 1/1992 | Kwoh |
| 5,079,699 A | 1/1992 | Tuy et al. |
| 5,086,401 A | 2/1992 | Glassman et al. |
| 5,094,241 A | 3/1992 | Allen |
| 5,097,839 A | 3/1992 | Allen |
| 5,098,426 A | 3/1992 | Sklar et al. |
| 5,099,845 A | 3/1992 | Besz et al. |
| 5,099,846 A | 3/1992 | Hardy |
| 5,105,829 A | 4/1992 | Fabian et al. |
| 5,107,839 A | 4/1992 | Houdek et al. |
| 5,107,843 A | 4/1992 | Aarnio et al. |
| 5,107,862 A | 4/1992 | Fabian et al. |
| 5,109,194 A | 4/1992 | Cantaloube |
| 5,119,817 A | 6/1992 | Allen |
| 5,142,930 A | 9/1992 | Allen et al. |
| 5,143,076 A | 9/1992 | Hardy et al. |
| 5,152,288 A | 10/1992 | Hoenig et al. |
| 5,160,337 A | 11/1992 | Cosman |
| 5,161,536 A | 11/1992 | Vilkomerson et al. |
| 5,170,789 A | 12/1992 | Narayan et al. |
| 5,178,164 A | 1/1993 | Allen |
| 5,178,621 A | 1/1993 | Cook et al. |
| 5,186,174 A | 2/1993 | Schlondorff et al. |
| 5,187,475 A | 2/1993 | Wagener et al. |
| 5,188,126 A | 2/1993 | Fabian et al. |
| 5,190,059 A | 3/1993 | Fabian et al. |
| 5,193,106 A | 3/1993 | DeSena |
| 5,197,476 A | 3/1993 | Nowacki et al. |
| 5,197,965 A | 3/1993 | Cherry et al. |
| 5,198,768 A | 3/1993 | Keren |
| 5,198,877 A | 3/1993 | Schulz |
| 5,206,589 A * | 4/1993 | Kado ............... G01R 33/0206 324/248 |
| 5,207,688 A | 5/1993 | Carol |
| 5,211,164 A | 5/1993 | Allen |
| 5,211,165 A | 5/1993 | Dumoulin et al. |
| 5,211,176 A | 5/1993 | Ishiguro et al. |
| 5,212,720 A | 5/1993 | Landi et al. |
| 5,214,615 A | 5/1993 | Bauer |
| 5,219,351 A | 6/1993 | Teubner et al. |
| 5,222,499 A | 6/1993 | Allen et al. |
| 5,224,049 A | 6/1993 | Mushabac |
| 5,228,442 A | 7/1993 | Imran |
| 5,230,338 A | 7/1993 | Allen et al. |
| 5,230,623 A | 7/1993 | Guthrie et al. |
| 5,233,990 A | 8/1993 | Barnea |
| 5,237,996 A | 8/1993 | Waldman et al. |
| 5,249,581 A | 10/1993 | Horbal et al. |
| 5,251,127 A | 10/1993 | Raab |
| 5,251,635 A | 10/1993 | Dumoulin et al. |
| 5,253,647 A | 10/1993 | Takahashi et al. |
| 5,255,680 A | 10/1993 | Darrow et al. |
| 5,257,636 A | 11/1993 | White |
| 5,257,998 A | 11/1993 | Ota et al. |
| 5,261,404 A | 11/1993 | Mick et al. |
| 5,265,610 A | 11/1993 | Darrow et al. |
| 5,265,611 A | 11/1993 | Hoenig et al. |
| 5,269,759 A | 12/1993 | Hernandez et al. |
| 5,271,400 A | 12/1993 | Dumoulin et al. |
| 5,273,025 A | 12/1993 | Sakiyama et al. |
| 5,274,551 A | 12/1993 | Corby, Jr. |
| 5,279,309 A | 1/1994 | Taylor et al. |
| 5,285,787 A | 2/1994 | Machida |
| 5,291,199 A | 3/1994 | Overman et al. |
| 5,291,889 A | 3/1994 | Kenet et al. |
| 5,295,483 A | 3/1994 | Nowacki et al. |
| 5,297,549 A | 3/1994 | Beatty et al. |
| 5,299,253 A | 3/1994 | Wessels |
| 5,299,254 A | 3/1994 | Dancer et al. |
| 5,299,288 A | 3/1994 | Glassman et al. |
| 5,300,080 A | 4/1994 | Clayman et al. |
| 5,305,091 A | 4/1994 | Gelbart et al. |
| 5,305,203 A | 4/1994 | Raab |
| 5,306,271 A | 4/1994 | Zinreich et al. |
| 5,307,072 A | 4/1994 | Jones, Jr. |
| 5,309,913 A | 5/1994 | Kormos et al. |
| 5,315,630 A | 5/1994 | Sturm et al. |
| 5,316,024 A | 5/1994 | Hirschi et al. |
| 5,318,025 A | 6/1994 | Dumoulin et al. |
| 5,320,111 A | 6/1994 | Livingston |
| 5,325,728 A | 7/1994 | Zimmerman et al. |
| 5,325,873 A | 7/1994 | Hirschi et al. |
| 5,329,944 A | 7/1994 | Fabian et al. |
| 5,330,485 A | 7/1994 | Clayman et al. |
| 5,333,168 A | 7/1994 | Fernandes et al. |
| 5,353,795 A | 10/1994 | Souza et al. |
| 5,353,800 A | 10/1994 | Pohndorf et al. |
| 5,353,807 A | 10/1994 | DeMarco |
| 5,359,417 A | 10/1994 | Muller et al. |
| 5,368,030 A | 11/1994 | Zinreich et al. |
| 5,371,778 A | 12/1994 | Yanof et al. |
| 5,375,596 A | 12/1994 | Twiss et al. |
| 5,377,678 A | 1/1995 | Dumoulin et al. |
| 5,383,454 A | 1/1995 | Bucholz |
| 5,385,146 A | 1/1995 | Goldreyer |
| 5,385,148 A | 1/1995 | Lesh et al. |
| 5,386,828 A | 2/1995 | Owens et al. |
| 5,389,101 A | 2/1995 | Heilbrun et al. |
| 5,391,199 A | 2/1995 | Ben-Haim |
| 5,394,457 A | 2/1995 | Leibinger et al. |
| 5,394,875 A | 3/1995 | Lewis et al. |
| 5,397,329 A | 3/1995 | Allen |
| 5,398,684 A | 3/1995 | Hardy |
| 5,399,146 A | 3/1995 | Nowacki et al. |
| 5,400,384 A | 3/1995 | Fernandes et al. |
| 5,402,801 A | 4/1995 | Taylor |
| 5,408,409 A | 4/1995 | Glassman et al. |
| 5,413,573 A | 5/1995 | Koivukangas |
| 5,417,210 A | 5/1995 | Funda et al. |
| 5,419,325 A | 5/1995 | Dumoulin et al. |
| 5,423,334 A | 6/1995 | Jordan |
| 5,425,367 A | 6/1995 | Shapiro et al. |
| 5,425,382 A | 6/1995 | Golden et al. |
| 5,426,683 A | 6/1995 | O'Farrell, Jr. et al. |
| 5,426,687 A | 6/1995 | Goodall et al. |
| 5,427,097 A | 6/1995 | Depp |

(56) References Cited

U.S. PATENT DOCUMENTS

| | | |
|---|---|---|
| 5,429,132 A | 7/1995 | Guy et al. |
| 5,433,198 A | 7/1995 | Desai |
| RE35,025 E | 8/1995 | Anderton |
| 5,437,277 A | 8/1995 | Dumoulin et al. |
| 5,443,066 A | 8/1995 | Dumoulin et al. |
| 5,443,489 A | 8/1995 | Ben-Haim |
| 5,444,756 A | 8/1995 | Pai et al. |
| 5,445,144 A | 8/1995 | Wodicka et al. |
| 5,445,150 A | 8/1995 | Dumoulin et al. |
| 5,445,166 A | 8/1995 | Taylor |
| 5,446,548 A | 8/1995 | Gerig et al. |
| 5,447,154 A | 9/1995 | Cinquin et al. |
| 5,448,610 A | 9/1995 | Yamamoto et al. |
| 5,453,686 A | 9/1995 | Anderson |
| 5,456,718 A | 10/1995 | Szymaitis |
| 5,457,641 A | 10/1995 | Zimmer et al. |
| 5,458,718 A | 10/1995 | Venkitachalam |
| 5,464,446 A | 11/1995 | Dreessen et al. |
| 5,465,714 A | 11/1995 | Scheuing |
| 5,469,847 A | 11/1995 | Zinreich et al. |
| 5,478,341 A | 12/1995 | Cook et al. |
| 5,478,343 A | 12/1995 | Ritter |
| 5,480,422 A | 1/1996 | Ben-Haim |
| 5,480,439 A | 1/1996 | Bisek et al. |
| 5,483,951 A | 1/1996 | Frassica et al. |
| 5,483,961 A | 1/1996 | Kelly et al. |
| 5,485,849 A | 1/1996 | Panescu et al. |
| 5,487,391 A | 1/1996 | Panescu |
| 5,487,729 A | 1/1996 | Avellanet et al. |
| 5,487,757 A | 1/1996 | Truckai et al. |
| 5,490,196 A | 2/1996 | Rudich et al. |
| 5,494,034 A | 2/1996 | Schlondorff et al. |
| 5,503,416 A | 4/1996 | Aoki et al. |
| 5,513,637 A | 5/1996 | Twiss et al. |
| 5,514,146 A | 5/1996 | Lam et al. |
| 5,515,160 A | 5/1996 | Schulz et al. |
| 5,517,990 A | 5/1996 | Kalfas et al. |
| 5,531,227 A | 7/1996 | Schneider |
| 5,531,520 A | 7/1996 | Grimson et al. |
| 5,542,938 A | 8/1996 | Avellanet et al. |
| 5,543,951 A | 8/1996 | Moehrmann |
| 5,546,940 A | 8/1996 | Panescu et al. |
| 5,546,949 A | 8/1996 | Frazin et al. |
| 5,546,951 A | 8/1996 | Ben-Haim |
| 5,551,429 A | 9/1996 | Fitzpatrick et al. |
| 5,558,091 A | 9/1996 | Acker et al. |
| 5,566,681 A | 10/1996 | Manwaring et al. |
| 5,568,384 A | 10/1996 | Robb et al. |
| 5,568,809 A | 10/1996 | Ben-haim |
| 5,572,999 A | 11/1996 | Funda et al. |
| 5,573,533 A | 11/1996 | Strul |
| 5,575,794 A | 11/1996 | Walus et al. |
| 5,575,798 A | 11/1996 | Koutrouvelis |
| 5,583,909 A | 12/1996 | Hanover |
| 5,588,430 A | 12/1996 | Bova et al. |
| 5,590,215 A | 12/1996 | Allen |
| 5,592,939 A | 1/1997 | Martinelli |
| 5,595,193 A | 1/1997 | Walus et al. |
| 5,596,228 A | 1/1997 | Anderton et al. |
| 5,600,330 A | 2/1997 | Blood |
| 5,603,318 A | 2/1997 | Heilbrun et al. |
| 5,611,025 A | 3/1997 | Lorensen et al. |
| 5,617,462 A | 4/1997 | Spratt |
| 5,617,857 A | 4/1997 | Chader et al. |
| 5,619,261 A | 4/1997 | Anderton |
| 5,622,169 A | 4/1997 | Golden et al. |
| 5,622,170 A | 4/1997 | Schulz |
| 5,627,873 A | 5/1997 | Hanover et al. |
| 5,628,315 A | 5/1997 | Vilsmeier et al. |
| 5,630,431 A | 5/1997 | Taylor |
| 5,636,644 A | 6/1997 | Hart et al. |
| 5,638,819 A | 6/1997 | Manwaring et al. |
| 5,640,170 A | 6/1997 | Anderson |
| 5,642,395 A | 6/1997 | Anderton et al. |
| 5,643,268 A | 7/1997 | Vilsmeier et al. |
| 5,645,065 A | 7/1997 | Shapiro et al. |
| 5,646,524 A | 7/1997 | Gilboa |
| 5,647,361 A | 7/1997 | Damadian |
| 5,662,111 A | 9/1997 | Cosman |
| 5,664,001 A | 9/1997 | Tachibana et al. |
| 5,669,801 A | 9/1997 | Lee |
| 5,674,296 A | 10/1997 | Bryan et al. |
| 5,676,673 A | 10/1997 | Ferre et al. |
| 5,681,260 A | 10/1997 | Ueda et al. |
| 5,682,886 A | 11/1997 | Delp et al. |
| 5,682,890 A | 11/1997 | Kormos et al. |
| 5,690,108 A | 11/1997 | Chakeres |
| 5,694,945 A | 12/1997 | Ben-Haim |
| 5,695,500 A | 12/1997 | Taylor et al. |
| 5,695,501 A | 12/1997 | Carol et al. |
| 5,696,500 A | 12/1997 | Diem |
| 5,697,377 A | 12/1997 | Wittkampf |
| 5,702,406 A | 12/1997 | Vilsmeier et al. |
| 5,711,299 A | 1/1998 | Manwaring et al. |
| 5,713,946 A | 2/1998 | Ben-Haim |
| 5,715,822 A | 2/1998 | Watkins et al. |
| 5,715,836 A | 2/1998 | Kliegis et al. |
| 5,718,241 A | 2/1998 | Ben-Haim et al. |
| 5,727,552 A | 3/1998 | Ryan |
| 5,727,553 A | 3/1998 | Saad |
| 5,729,129 A | 3/1998 | Acker |
| 5,730,129 A | 3/1998 | Darrow et al. |
| 5,730,130 A | 3/1998 | Fitzpatrick et al. |
| 5,732,703 A | 3/1998 | Kalfas et al. |
| 5,735,278 A | 4/1998 | Hoult et al. |
| 5,738,096 A | 4/1998 | Ben-Haim |
| 5,740,802 A | 4/1998 | Nafis et al. |
| 5,740,808 A | 4/1998 | Panescu et al. |
| 5,741,214 A | 4/1998 | Ouchi et al. |
| 5,742,394 A | 4/1998 | Hansen |
| 5,744,953 A | 4/1998 | Hansen |
| 5,748,767 A | 5/1998 | Raab |
| 5,749,362 A | 5/1998 | Funda et al. |
| 5,749,835 A | 5/1998 | Glantz |
| 5,752,513 A | 5/1998 | Acker et al. |
| 5,752,976 A | 5/1998 | Duffin et al. |
| 5,755,725 A | 5/1998 | Druais |
| RE35,816 E | 6/1998 | Schulz |
| 5,758,667 A | 6/1998 | Slettenmark |
| 5,760,335 A | 6/1998 | Gilboa |
| 5,762,064 A | 6/1998 | Polvani |
| 5,767,669 A | 6/1998 | Hansen et al. |
| 5,767,960 A | 6/1998 | Orman |
| 5,769,789 A | 6/1998 | Wang et al. |
| 5,769,843 A | 6/1998 | Abela et al. |
| 5,769,861 A | 6/1998 | Vilsmeier |
| 5,772,594 A | 6/1998 | Barrick |
| 5,775,322 A | 7/1998 | Silverstein et al. |
| 5,776,064 A | 7/1998 | Kalfas et al. |
| 5,777,720 A * | 7/1998 | Shapiro et al. ............... 351/237 |
| 5,782,765 A | 7/1998 | Jonkman |
| 5,787,886 A * | 8/1998 | Kelly et al. .................. 600/407 |
| 5,792,055 A | 8/1998 | McKinnon |
| 5,795,294 A | 8/1998 | Luber et al. |
| 5,797,849 A | 8/1998 | Vesely et al. |
| 5,799,055 A | 8/1998 | Peshkin et al. |
| 5,799,099 A | 8/1998 | Wang et al. |
| 5,800,352 A | 9/1998 | Ferre et al. |
| 5,800,535 A | 9/1998 | Howard, III |
| 5,802,719 A | 9/1998 | O'Farrell, Jr. et al. |
| 5,803,089 A | 9/1998 | Ferre et al. |
| 5,807,252 A | 9/1998 | Hassfeld et al. |
| 5,810,008 A | 9/1998 | Dekel et al. |
| 5,810,728 A | 9/1998 | Kuhn |
| 5,810,735 A | 9/1998 | Halperin et al. |
| 5,820,553 A | 10/1998 | Hughes |
| 5,823,192 A | 10/1998 | Kalend et al. |
| 5,823,958 A | 10/1998 | Truppe |
| 5,828,725 A | 10/1998 | Levinson |
| 5,828,770 A | 10/1998 | Leis et al. |
| 5,829,444 A | 11/1998 | Ferre et al. |
| 5,831,260 A | 11/1998 | Hansen |
| 5,833,608 A | 11/1998 | Acker |
| 5,834,759 A | 11/1998 | Glossop |

(56) References Cited

U.S. PATENT DOCUMENTS

| | | |
|---|---|---|
| 5,836,954 A | 11/1998 | Heilbrun et al. |
| 5,840,024 A | 11/1998 | Taniguchi et al. |
| 5,840,025 A | 11/1998 | Ben-Haim |
| 5,843,076 A | 12/1998 | Webster, Jr. et al. |
| 5,848,967 A | 12/1998 | Cosman |
| 5,851,183 A | 12/1998 | Bucholz |
| 5,865,846 A | 2/1999 | Bryan et al. |
| 5,868,674 A | 2/1999 | Glowinski et al. |
| 5,868,675 A | 2/1999 | Henrion et al. |
| 5,871,445 A | 2/1999 | Bucholz |
| 5,871,455 A | 2/1999 | Ueno |
| 5,871,487 A | 2/1999 | Warner et al. |
| 5,873,822 A | 2/1999 | Ferre et al. |
| 5,882,304 A | 3/1999 | Ehnholm et al. |
| 5,884,410 A | 3/1999 | Prinz |
| 5,889,834 A | 3/1999 | Vilsmeier et al. |
| 5,891,034 A | 4/1999 | Bucholz |
| 5,891,157 A | 4/1999 | Day et al. |
| 5,904,691 A | 5/1999 | Barnett et al. |
| 5,907,395 A | 5/1999 | Schulz et al. |
| 5,913,820 A | 6/1999 | Bladen et al. |
| 5,920,395 A | 7/1999 | Schulz |
| 5,921,992 A | 7/1999 | Costales et al. |
| 5,923,727 A | 7/1999 | Navab |
| 5,928,248 A | 7/1999 | Acker |
| 5,938,603 A | 8/1999 | Ponzi |
| 5,938,694 A | 8/1999 | Jaraczewski et al. |
| 5,947,980 A | 9/1999 | Jensen et al. |
| 5,947,981 A | 9/1999 | Cosman |
| 5,950,629 A | 9/1999 | Taylor et al. |
| 5,951,475 A | 9/1999 | Gueziec et al. |
| 5,951,571 A | 9/1999 | Audette |
| 5,954,647 A | 9/1999 | Bova et al. |
| 5,954,796 A | 9/1999 | McCarty et al. |
| 5,957,844 A | 9/1999 | Dekel et al. |
| 5,967,980 A | 10/1999 | Ferre et al. |
| 5,967,982 A | 10/1999 | Barnett |
| 5,968,047 A | 10/1999 | Reed |
| 5,971,997 A | 10/1999 | Guthrie et al. |
| 5,976,156 A | 11/1999 | Taylor et al. |
| 5,980,535 A | 11/1999 | Barnett et al. |
| 5,983,126 A | 11/1999 | Wittkampf |
| 5,987,349 A | 11/1999 | Schulz |
| 5,987,960 A | 11/1999 | Messner et al. |
| 5,999,837 A | 12/1999 | Messner et al. |
| 5,999,840 A | 12/1999 | Grimson et al. |
| 6,001,130 A | 12/1999 | Bryan et al. |
| 6,006,126 A | 12/1999 | Cosman |
| 6,006,127 A | 12/1999 | Van Der Brug et al. |
| 6,013,087 A | 1/2000 | Adams et al. |
| 6,014,580 A | 1/2000 | Blume et al. |
| 6,016,439 A | 1/2000 | Acker |
| 6,019,725 A | 2/2000 | Vesely et al. |
| 6,024,695 A | 2/2000 | Taylor et al. |
| 6,050,724 A | 4/2000 | Schmitz et al. |
| 6,059,718 A | 5/2000 | Taniguchi et al. |
| 6,063,022 A | 5/2000 | Ben-Haim |
| 6,071,288 A | 6/2000 | Carol et al. |
| 6,073,043 A | 6/2000 | Schneider |
| 6,076,008 A | 6/2000 | Bucholz |
| 6,096,050 A | 8/2000 | Audette |
| 6,104,944 A | 8/2000 | Martinelli |
| 6,118,845 A | 9/2000 | Simon et al. |
| 6,122,538 A | 9/2000 | Sliwa, Jr. et al. |
| 6,122,541 A | 9/2000 | Cosman et al. |
| 6,131,396 A | 10/2000 | Duerr et al. |
| 6,139,183 A | 10/2000 | Graumann |
| 6,147,480 A | 11/2000 | Osadchy et al. |
| 6,149,592 A | 11/2000 | Yanof et al. |
| 6,156,067 A | 12/2000 | Bryan et al. |
| 6,161,032 A | 12/2000 | Acker |
| 6,165,181 A | 12/2000 | Heilbrun et al. |
| 6,167,296 A | 12/2000 | Shahidi |
| 6,172,499 B1 | 1/2001 | Ashe |
| 6,175,756 B1 * | 1/2001 | Ferre et al. .................. 600/424 |
| 6,178,345 B1 | 1/2001 | Vilsmeier et al. |
| 6,194,639 B1 | 2/2001 | Botella et al. |
| 6,201,387 B1 | 3/2001 | Govari |
| 6,201,987 B1 | 3/2001 | Dumoulin |
| 6,203,497 B1 | 3/2001 | Dekel et al. |
| 6,211,666 B1 | 4/2001 | Acker |
| 6,223,067 B1 | 4/2001 | Vilsmeier et al. |
| 6,225,805 B1 | 5/2001 | Damadian et al. |
| 6,233,476 B1 | 5/2001 | Strommer et al. |
| 6,246,231 B1 | 6/2001 | Ashe |
| 6,259,942 B1 | 7/2001 | Westermann et al. |
| 6,273,896 B1 | 8/2001 | Franck et al. |
| 6,285,902 B1 | 9/2001 | Kienzle, III et al. |
| 6,298,262 B1 | 10/2001 | Franck et al. |
| 6,314,310 B1 * | 11/2001 | Ben-Haim ............ A61B 90/36 600/424 |
| 6,332,089 B1 | 12/2001 | Acker et al. |
| 6,341,231 B1 | 1/2002 | Ferre et al. |
| 6,351,659 B1 | 2/2002 | Vilsmeier |
| 6,352,363 B1 | 3/2002 | Munger et al. |
| 6,381,485 B1 | 4/2002 | Hunter et al. |
| 6,424,856 B1 | 7/2002 | Vilsmeier et al. |
| 6,427,079 B1 | 7/2002 | Schneider et al. |
| 6,427,314 B1 | 8/2002 | Acker |
| 6,428,547 B1 | 8/2002 | Vilsmeier et al. |
| 6,434,415 B1 | 8/2002 | Foley et al. |
| 6,437,567 B1 | 8/2002 | Schenck et al. |
| 6,445,943 B1 | 9/2002 | Ferre et al. |
| 6,470,207 B1 | 10/2002 | Simon et al. |
| 6,474,341 B1 | 11/2002 | Hunter et al. |
| 6,478,802 B2 | 11/2002 | Kienzle, III et al. |
| 6,484,049 B1 | 11/2002 | Seeley et al. |
| 6,484,118 B1 * | 11/2002 | Govari ..................... A61B 5/06 702/150 |
| 6,490,475 B1 | 12/2002 | Seeley et al. |
| 6,493,573 B1 | 12/2002 | Martinelli et al. |
| 6,498,944 B1 | 12/2002 | Ben-Haim et al. |
| 6,499,488 B1 | 12/2002 | Hunter et al. |
| 6,516,046 B1 | 2/2003 | Frohlich et al. |
| 6,527,443 B1 | 3/2003 | Vilsmeier et al. |
| 6,551,325 B2 | 4/2003 | Neubauer et al. |
| 6,584,174 B2 | 6/2003 | Schubert et al. |
| 6,593,884 B1 | 7/2003 | Gilboa et al. |
| 6,609,022 B2 | 8/2003 | Vilsmeier et al. |
| 6,611,700 B1 | 8/2003 | Vilsmeier et al. |
| 6,636,757 B1 * | 10/2003 | Jascob ................... A61B 19/52 324/207.11 |
| 6,640,128 B2 | 10/2003 | Vilsmeier et al. |
| 6,694,162 B2 | 2/2004 | Hartlep |
| 6,701,179 B1 | 3/2004 | Martinelli et al. |
| 2001/0007918 A1 | 7/2001 | Vilsmeier et al. |
| 2002/0095081 A1 | 7/2002 | Vilsmeier |
| 2004/0024309 A1 | 2/2004 | Ferre et al. |
| 2004/0116803 A1 | 6/2004 | Jascob et al. |

FOREIGN PATENT DOCUMENTS

| | | |
|---|---|---|
| DE | 3508730 | 9/1986 |
| DE | 3717871 | 12/1988 |
| DE | 3831278 A1 | 3/1989 |
| DE | 3838011 | 7/1989 |
| DE | 4213426 A1 | 10/1992 |
| DE | 4225112 | 12/1993 |
| DE | 4233978 | 4/1994 |
| DE | 19715202 | 10/1998 |
| DE | 19751761 | 10/1998 |
| DE | 19832296 | 2/1999 |
| DE | 19747427 | 5/1999 |
| DE | 10085137 | 11/2002 |
| EP | 0062941 | 10/1982 |
| EP | 0119660 | 9/1984 |
| EP | 0155857 | 9/1985 |
| EP | 0319844 | 6/1989 |
| EP | 0326768 | 8/1989 |
| EP | 0350996 A1 | 1/1990 |
| EP | 0419729 A1 | 4/1991 |
| EP | 0427358 | 5/1991 |
| EP | 0456103 | 11/1991 |
| EP | 0581704 | 2/1994 |

(56) References Cited

FOREIGN PATENT DOCUMENTS

| | | |
|---|---|---|
| EP | 0651968 | 5/1995 |
| EP | 0655138 | 5/1995 |
| EP | 0894473 A2 | 2/1999 |
| EP | 0908146 | 4/1999 |
| EP | 0930046 | 7/1999 |
| EP | 0993804 A1 | 4/2000 |
| FR | 2417970 | 9/1979 |
| FR | 2618211 | 1/1989 |
| GB | 2094590 A | 9/1982 |
| GB | 2164856 | 4/1986 |
| JP | 62327 | 6/1985 |
| JP | 2765738 | 6/1988 |
| JP | 63240851 | 10/1988 |
| JP | 3267054 | 11/1991 |
| JP | 6194639 | 7/1994 |
| WO | WO-8809151 | 12/1988 |
| WO | WO-8905123 | 6/1989 |
| WO | WO-9005494 A1 | 5/1990 |
| WO | WO-9103982 | 4/1991 |
| WO | WO-9104711 | 4/1991 |
| WO | WO-9107726 | 5/1991 |
| WO | WO-9203090 | 3/1992 |
| WO | WO-9206645 | 4/1992 |
| WO | WO-9404938 | 3/1994 |
| WO | WO-9423647 | 10/1994 |
| WO | WO-9424933 | 11/1994 |
| WO | WO-9507055 A1 | 3/1995 |
| WO | WO-9611624 | 4/1996 |
| WO | WO-9632059 A1 | 10/1996 |
| WO | WO-9736192 A1 | 10/1997 |
| WO | WO-9749453 A1 | 12/1997 |
| WO | WO-9808554 | 3/1998 |
| WO | WO-9838908 | 9/1998 |
| WO | WO-9927839 | 12/1998 |
| WO | WO-9915097 A2 | 4/1999 |
| WO | WO-9921498 A1 | 5/1999 |
| WO | WO-9923956 A1 | 5/1999 |
| WO | WO-9926549 A1 | 6/1999 |
| WO | WO-9929253 A1 | 6/1999 |
| WO | WO-9933406 A1 | 7/1999 |
| WO | WO-9937208 A1 | 7/1999 |
| WO | WO-9938449 A1 | 8/1999 |
| WO | WO-9952094 A1 | 10/1999 |
| WO | WO-9960939 | 12/1999 |
| WO | WO-0010456 A1 | 3/2000 |
| WO | WO-0130256 A1 | 5/2001 |
| WO | WO-0130437 | 5/2001 |

OTHER PUBLICATIONS

Adams et al., "Orientation Aid for Head and Neck Surgeons," Innov. Tech. Biol. Med., vol. 13, No. 4, 1992, pp. 409-424.
Adams et al., Computer-Assisted Surgery, IEEE Computer Graphics & Applications, pp. 43-45 , (May 1990).
Barrick et al., "Prophylactic Intramedullary Fixation of the Tibia for Stress Fracture in a Professional Athlete," Journal of Orthopaedic Trauma, vol. 6, No. 2, pp. 241-244 (1992).
Barrick et al., "Technical Difficulties with the Brooker-Wills Nail in Acute Fractures of the Femur," Journal of Orthopaedic Trauma, vol. 6, No. 2, pp. 144-150 (1990).
Barrick, "Distal Locking Screw Insertion Using a Cannulated Drill Bit: Technical Note," Journal of Orthopaedic Trauma, vol. 7, No. 3, 1993, pp. 248-251.
Batnitzky et al., "Three-Dimensinal Computer Reconstructions of Brain Lesions from Surface Contours Provided by Computed Tomography: A Prospectus," Neurosurgery, vol. 11, No. 1, Part 1, 1982, pp. 73-84.
Benzel et al., "Magnetic Source Imaging: a Review of the Magnes System of Biomagnetic Technologies Incorporated," Neurosurgery, vol. 33, No. 2 (Aug. 1993), pp. 252-259.
Bergstrom et al. Stereotaxic Computed Tomography, Am. J. Roentgenol, vol. 127 pp. I 67-I 170 (1976).
Bouazza-Marouf et al.; "Robotic-Assisted Internal Fixation of Femoral Fractures", IMECHE., pp. 51-58 (1995).
Brack et al., "Accurate X-ray Based Navigation in Computer-Assisted Orthopedic Surgery," CAR '98, pp. 716-722.
Brown, R., M.D., A Stereotactic Head Frame for Use with CT Body Scanners, Investigative Radiology@: J.B. Lippincott Company, pp. 300-304 (Jul.-Aug. 1979).
Bryan, "Bryan Cervical Disc System Single Level Surgical Technique", Spinal Dynamics, 2002, pp. 1-33.
Bucholz et al., "Variables affecting the accuracy of stereotactic localizationusing computerized tomography," Journal of Neurosurgery, vol. 79, Nov. 1993, pp. 667-673.
Bucholz, R.D., et al. Image-guided surgical techniques for infections and trauma of the central nervous system, Neurosurg. Clinics of N.A., vol. 7. No. 2, pp. 187-200 (1996).
Bucholz, R.D., et al., A Comparison of Sonic Digitizers Versus Light Emitting Diode-Based Localization, Interactive Image-Guided Neurosurgery, Chapter 16, pp. 179-200 (1993).
Bucholz, R.D., et al., Intraoperative localization using a three dimensional optical digitizer, SPIE—The Intl. Soc. for Opt. Eng., vol. 1894, pp. 312-322 (Jan. 17-19, 1993).
Bucholz, R.D., et al., The Correction of Stereotactic Inaccuracy Caused by Brain Shift Using an Intraoperative Ultrasound Device, First Joint Conference, Computer Vision, Virtual Reality and Robotics in Medicine and Medical Robotics and Computer-Assisted Surgery, Grenoble, France, pp. 459-466 (Mar. 19-22, 1997).
Champleboux et al., "Accurate Calibration of Cameras and Range Imaging Sensors: the NPBS Method," IEEE International Conference on Robotics and Automation, Nice, France, May 1992.
Champleboux, "Utilisation de Fonctions Splines pour la Mise au Point D'un Capteur Tridimensionnel sans Contact," Quelques Applications Medicales, Jul. 1991.
Cinquin et al., "Computer Assisted Medical Interventions," IEEE Engineering in Medicine and Biology, May/Jun. 1995, pp. 254-263.
Cinquin et al., "Computer Assisted Medical Interventions," International Advanced Robotics Programme, Sep. 1989, pp. 63-65.
Clarysse et al., "A Computer-Assisted System for 3-D Frameless ocalization in Stereotaxic MRI," IEEE Transactions on Medical Imaging, vol. 10, No. 4, Dec. 1991, pp. 523-529.
Cutting M.D. et al., Optical Tracking of Bone Fragments During Craniofacial Surgery, Second Annual International Symposium on Medical Robotics and Computer Assisted Surgery, pp. 221-225, (Nov. 1995).
European Office Action mailed Aug. 14, 2009 for EP00972378 claiming benefit of PCT/US2000/029721, filed Oct. 27, 2000, which is based on U.S. Appl. No. 09/589,779, filed Jun. 8, 2000, which claims priority from U.S. Appl. No. 60/161,991, filed Oct. 28, 1999.
Feldmar et al., "3D-2D Projective Registration of Free-Form Curves and Surfaces," Rapport de recherche (Inria Sophia Antipolis), 1994, pp. 1-44.
Foley et al., "Fundamentals of Interactive Computer Graphics." The Systems Programming Series, Chapter 7, Jul. 1984, pp. 245-266.
Foley et al., "Image-guided Intraoperative Spinal Localization," Intraoperative Neuroprotection, Chapter 19, 1996, pp. 325-340.
Foley, "The StealthStation: Three-Dimensional Image-Interactive Guidance o the Spine Surgeon," Spinal Frontiers, Apr. 1996, pp. 7-9.
Friets, E.M., et al. A Frameless Stereotaxic Operating Microscope for Neurosurgery, IEEE Trans. on Biomed. Eng., vol. 36, No. 6, pp. 608-617 (Jul. 1989).
Gallen, C.C., et al., Intracranial Neurosurgery Guided by Functional Imaging, Surg. Neurol., vol. 42, pp. 523-530 (1994).
Galloway, R.L., et al., Interactive Image-Guided Neurosurgery, IEEE Trans. on Biomed. Eng., vol. 89, No. 12, pp. 1226-1231 (1992).
Germano, "Instrumentation, Technique and Technology", Neurosurgery, vol. 37, No. 2, Aug. 1995, pp. 348-350.
Gildenberg et al., "Calculation of Stereotactic Coordinates from the Computed Tomographic Scan," Neurosurgery, vol. 10, No. 5, May 1982, pp. 580-586.
Gomez, C.R., et al., Transcranial Doppler Ultrasound Following Closed Head Injury: Vasospasm or Vasoparalysis?, Surg. Neurol., vol. 35, pp. 30-35 (1991).

(56) References Cited

OTHER PUBLICATIONS

Gonzalez, "Digital Image Fundamentals," Digital Image Processing, Second Edition, 1987, pp. 52-54.
Gottesfeld Brown et al., "Registration of Planar Film Radiographs with Computer Tomography," Proceedings of MMBIA, Jun. 1996, pp. 42-51.
Grimson, W.E.L., An Automatic Registration Method for Frameless Stereotaxy, Image Guided Surgery, and enhanced Reality Visualization, IEEE, pp. 430-436 (1994).
Grimson, W.E.L., et al., Virtual-reality technology is giving surgeons the equivalent of x-ray vision helping them to remove tumors more effectively, to minimize surgical wounds and to avoid damaging critical tissues, Sci. Amer., vol. 280, No. 6, pp. 62-69 (Jun. 1999).
Gueziec et al., "Registration of Computed Tomography Data to a Surgical Robot Using Fluoroscopy: A Feasibility Study," Computer Science/Mathematics, Sep. 27, 1996, 6 pages.
Hamadeh et al., "Automated 3-Dimensional Computed Tomographic and Fluorscopic Image Registration," Computer Aided Surgery (1998), 3:11-19.
Hamadeh et al., "Towards Automatic Registration Between CT and X-ray Images: Cooperation Between 3D/2D Registration and 2D Edge Detection," MRCAS '95, pp. 39-46.
Hardy, T., M.D., et al., CASS: A Program for Computer Assisted Stereotaxic Surgery, The Fifth Annual Symposium on Comptuer Applications in Medical Care, Proceedings, Nov. 1-4, 1981, IEEE, pp. 1116-1126, (1981).
Hatch, "Reference-Display System for the Integration of CT Scanning and the Operating Microscope," Thesis, Thayer School of Engineering, Oct. 1984, pp. 1-189.
Hatch, et al., "Reference-Display System for the Integration of CT Scanning and the Operating Microscope", Proceedings of the Eleventh Annual Northeast Bioengineering Conference, May 1985, pp. 252-254.
Heilbrun et al., "Preliminary experience with Brown-Roberts-Wells (BRW) computerized tomography stereotaxic guidance system," Journal of Neurosurgery, vol. 59, Aug. 1983, pp. 217-222.
Heilbrun, M.D., Progressive Technology Applications, Neurosurgery for the Third Milleniurn, Chapter 15, J. Whitaker & Sons, Ltd., Amer. Assoc. of Neurol. Surgeons, pp. 191-198 (1992).
Heilbrun, M.P., Computed Tomography-Guided Stereotactic Systems, Clinical Neurosurgery, Chapter 31, pp. 564-581 (1983).
Heilbrun, M.P., et at., Stereotactic Localization and Guidance Using a Machine Vision Technique, Sterotact & Funct. Neurosurg., Proceed. of the Mtg. of the Amer. Soc. for Sterot. and Funct. Neurosurg. (Pittsburgh, PA) vol. 58, pp. 94-98 (1992).
Henderson et al., "An Accurate and Ergonomic Method of Registration for Image-guided Neurosurgery," Computerized Medical Imaging and Graphics, vol. 18, No. 4, Jul.-Aug. 1994, pp. 273-277.
Hoerenz, "The Operating Microscope I. Optical Principles, Illumination Systems, and Support Systems," Journal of Microsurgery, vol. 1, 1980, pp. 364-369.
Hofstetter et al., "Fluoroscopy Based Surgical Navigation—Concept and Clinical Applications," Computer Assisted Radiology and Surgery, 1997, pp. 956-960.
Horner et al., "A Comparison of CT-Stereotaxic Brain Biopsy Techniques," Investigative Radiology, Sep.-Oct. 1984, pp. 367-373.
Hounsfield, "Computerized transverse axial scanning (tomography): Part 1. Description of system," British Journal of Radiology, vol. 46, No. 552, Dec. 1973, pp. 1016-1022.
International Preliminary Examination Report mailed Aug. 8, 2001 for PCT/US00/29721 claiming benefit of U.S. Appl. No. 09/589,779, filed Jun. 8, 2000.
International Search Report mailed Dec. 6, 2002 for PCT/US02/17228 claiming benefit of U.S. Appl. No. 09/873,604, filed Jun. 4, 2001.
International Search Report mailed Jan. 24, 2001 for PCT/US00/29721 which claims benefit of U.S. Appl. No. 09/589,779, filed Jun. 8, 2000.
Jacques et al., "A Computerized Microstereotactic Method to Approach, 3-Dimensionally Reconstruct, Remove and Adjuvantly Treat Small CNS Lesions," Applied Neurophysiology, vol. 43, 1980, pp. 176-182.
Jacques et al., "Computerized three-dimensional stereotaxic removal of small central nervous system lesion in patients," J. Neurosurg., vol. 53, Dec. 1980, pp. 816-820.
Joskowicz et al., "Computer-Aided Image-Guided Bone Fracture Surgery: Concept and Implementation," CAR '98, pp. 710-715.
Kall, B., The Impact of Computer and Imgaging Technology on Stereotactic Surgery, Proceedings of the Meeting of the American Society for Stereotactic and Functional Neurosurgery, pp. 10-22 (1987).
Kato, A., et at., A frameless, armless navigational system for computer-assisted neurosurgery, J. Neurosurg., vol. 74, pp. 845-849 (May 1991 ).
Kelly et al., "Computer-assisted stereotaxic laser resection of intra-axial brain neoplasms," , Journal of Neurosurgery, vol. 64, Mar. 1986, pp. 427-439.
Kelly et al., "Precision Resection of Intra-Axial CNS Lesions by CT-Based Stereotactic Craniotomy and Computer Monitored $CO_2$ Laser," Acta Neurochirurgica, vol. 68, 1983, pp. 1-9.
Kelly, P.J., Computer Assisted Stereotactic Biopsy and Volumetric Resection of Pediatric Brain Tumors, Brain Tumors in Children, Neurologic Clinics, vol. 9, No. 2, pp. 317-336 (May 1991).
Kelly, P.J., Computer-Directed Stereotactic Resection of Brain Tumors, Neurologica Operative Atlas, vol. 1, No. 4, pp. 299-313 (1991).
Kelly, P.J., et al., Results of Computed Tomography-based Computer-assisted Stereotactic Resection of Metastatic Intracranial Tumors, Neurosurgery, vol. 22, No. 1, Part 1, 1988, pp. 7-17 (Jan. 1988).
Kelly, P.J., Stereotactic Imaging, Surgical Planning and Computer-Assisted Resection of Intracranial Lesions: Methods and Results, Advances and Technical Standards in Neurosurgery, vol. 17, pp. 78-118, (1990).
Kim, W.S. et al., A Helmet Mounted Display for Telerobotics, IEEE, pp. 543-547 (1988).
Kosugi, Y., et at., An Articulated Neurosurgical Navigation System Using MRI and CT Images, IEEE Trans. on Biomed. Eng. vol. 35. No. 2, pp. 147-152 (Feb. 1988).
Krybus, W., et at., Navigation Support for Surgery by Means of Optical Position Detection, Computer Assisted Radiology Proceed. of the Intl. Symp. CAR '91 Computed Assisted Radiology, pp. 362-366 (Jul. 3-6, 1991).
Kwoh, Y.S., Ph.D., et al., A New Computerized Tomographic-AidedRobotic Stereotaxis System, Robotics Age, Vo1.7, No. 6, pp. 17-22 (Jun. 1985).
Laitinen et al., "An Adapter for Computed Tomography-Guided, Stereotaxis," Surg. Neurol., 1985, pp. 559-566.
Laitinen, "Noninvasive multipurpose stereoadapter," Neurological Research, Jun. 1987, pp. 137-141.
Lavallee et al, "Matching 3-D Smooth Surfaces with their 2-D Projections using 3-D Distance Maps," SPIE, vol. 1570, Geometric Methods in Computer Vision, 1991, pp. 322-336.
Lavallee et al., "Computer Assisted Driving of a Needle into the Brain," Proceedings of the International Symposium CAR '89, Computer Assisted Radiology, 1989, pp. 416-420.
Lavallee et al., "Computer Assisted Interventionist Imaging: The Instance of Stereotactic Brain Surgery," North-Holland MEDINFO 89, Part 1, 1989, pp. 613-617.
Lavallee et al., "Image guided operating robot: a clinical application in stereotactic neurosurgery," Proceedings of the 1992 IEEE Internation Conference on Robotics and Automation. May 1992, pp. 618-624.
Lavallee et al., "Matching of Medical Images for Computed and Robot Assisted Surgery," IEEE EMBS, Orlando, 1991.
Lavallee, "A New System for Computer Assisted Neurosurgery," IEEE Engineering in Medicine & Biology Society 11th Annual International Conference, 1989, pp. 0926-0927.
Lavallee, S., et al., Computer Assisted Knee Anterior Cruciate Ligament Reconstruction First Clinical Tests, Proceedings of the

(56) References Cited

OTHER PUBLICATIONS

First International Symposium on Medical Robotics and Computer Assisted Surgery, pp. 11-16 (Sep. 1994).
Lavallee, S., et al., Computer Assisted Medical Interventions, NATOAS8 Series, vol. F 60, 3d Imaging in Medic. DR. 301-312 (1990).
Leavitt, D.D., et al., Dynamic Field Shaping to Optimize Stereotactic Radiosurgery, I.J. Rad. I Onc. Biol. Physc., vol. 21, pp. 1247-1255 (1991).
Leksell et al., "Stereotaxis and Tomography—A Technical Note," ACTA Neurochirurgica, vol. 52, 1980, pp. 1-7.
Lemieux et al., "A Patient-to-Computed-Tomography Image Registration Method Based on Digitally Reconstructed Radiographs," Med. Phys. 21 (11), Nov. 1994, pp. 1749-1760.
Levin et al., "The Brain: Integrated Three-dimensional Display of MR and PET Images," Radiology, vol. 172, No. 3, Sep. 1989, pp. 783-789.
Maurer, J., et al., Registration of Head CT Images to Physical Space Using a Weighted Combination of Points and Surfaces, IEEE Trans. on Med. Imaging, vol. 17, No. 5, pp. 753-761 (Oct. 1998).
Mazier et al., "Computer-Assisted Interventionist Imaging: Application to the Vertebral Column Surgery," Annual International Conference of the IEEE Engineering in Medicine and Biology Society, vol. 12, No. 1, 1990, pp. 0430-0431.
Mazier et al., Chirurgie de la Colonne Vertebrale Assistee par Ordinateur: Appication au Vissage Pediculaire, Innov. Tech. Biol. Med., vol. 11, No. 5, 1990, pp. 559-566.
McGirr, S., M.D., et al., Stereotactic Resection of Juveinle Pilocytic Astrocytomas of the Thalamus and Basal Ganaglia, Neurosurgery, vol. 20, No. 3, pp. 447-452, (1987).
Ng, W.S. et al., Robotic Surgery—A First-Hand Experience in Transurethral Resection of the Prostate Surgery, IEEE Eng. in Med. and Biology, pp. 120-125 (Mar. 1993).
Pelizzari et al., "Accurate Three-Dimensional Registration of CT, PET, and/or MR Images of the Brain," Journal of Computer Assisted Tomography, Jan./Feb. 1989, pp. 20-26.
Pelizzari et al., "Interactive 3D Patient-Image Registration," Information Processing in Medical Imaging, 12th International Conference, IPMI Jul. 7-12, 1991, 136-141 (A.C.F. Colchester et al. eds. 1991).
Pelizzari et al., No. 528—"Three Dimensional Correlation of PET, CT and MRI Images," The Journal of Nuclear Medicine, vol. 28, No. 4, Apr. 1987, p. 682.
Penn, R.D., et al., Stereotactic Surgery with Image Processing of Computerized Tomographic Scans, Neurosurgery, vol. 3, No. 2, pp. 157-163 (Sep.-Oct. 1978).
Phillips et al., "Image Guided Orthopaedic Surgery Design and Analysis," Trans Inst. MC, vol. 17, No. 5, 1995, pp. 251-264.
Potamianos et al., "Intra-Operative Imaging Guidance for Keyhole Surgery Methodology and Calibration," First International Symposium on Medical Robotics and Computer Assisted Surgery, Sep. 22-24, 1994, pp. 98-104.
Reinhardt et al., "CT-Guided 'Real Time' Stereotaxy," ACTA Neurochirurgica, 1989.
Reinhardt H., et al., A Computer-Assisted Device for Intraoperative CT-Correlated Localization of Brain Tumors, pp. 51-58 (1988).
Reinhardt, H.F., et al., Mikrochirugische Entfernung tiefliegender GefaBmiBbildungen mit Hilfe der Sonar-Stereometrie (Microsurgical Removal of Deep-Seated Vascular Malformations Using Sonar Stereometry). Ultraschall in Med. 12, pp. 80-83 (1991).
Reinhardt, H.F., et al., Sonic Stereometry in Microsurgical Procedures for Deep-Seated Brain Tumors and Vascular Malformations, Neurosurgery, vol. 32, No. 1, pp. 51-57 (Jan. 1993).
Roberts et al., "A frameless stereotaxic integration of computerized tomographic imaging and the operating microscope," J. Neurosurg., vol. 65, Oct. 1986, pp. 545-549.
Rosenbaum et al., "Computerized Tomography Guided Stereotaxis: A New Approach," Applied Neurophysiology, vol. 43, No. 3-5, 1980, pp. 172-173.
Sautot, "Vissage Pediculaire Assiste Par Ordinateur," Sep. 20, 1994.
Schueler et al., "Correction of Image Intensifier Distortion for Three-Dimensional X-Ray Angiography," SPIE Medical Imaging 1995, vol. 2432, pp. 272-279.
Selvik et al., "A Roentgen Stereophotogrammetric System," Acta Radiolog ca Diagnosis, 1983, pp. 343-352.
Shelden et al., "Development of a computerized microsteroetaxic method for localization and removal of minute CNS lesions under direct 3-D vision," J. Neurosurg., vol. 52, 1980, pp. 21-27.
Simon, D.A., Accuracy Validation in Image-Guided Orthopaedic Surgery, Second Annual Intl. Symp. on Med. Rob. an Comp-Assisted surgery, MRCAS '95, pp. 185-192 (undated).
Smith et al., "Computer Methods for Improved Diagnostic Image Display Applied to Stereotactic Neurosurgery," Automedical, vol. 14, 1992, pp. 371-382.
Smith et al., "The Neurostation™—A Highly Accurate, Minimally Invasive Solution to Frameless Stereotactic Neurosurgery," Computerized Medical Imaging and Graphics, vol. 18, Jul.-Aug. 1994, pp. 247-256.
Smith, K.R., et al. Multimodality Image Analysis and Dispaly Methods for Improved Tumor Localization in Stereotactic Neurosurgery, Annul. Intl. Conf. of the IEEE Eng. in Med. and Bio. Soc., vol. 13, No. 1, p. 210 (1991).
Tan, K., Ph.D., et al., A frameless stereotactic approach to neurosurgical planning based on retrospective patient-image registration, J Neurosurgery, vol. 79, pp. 296-303 (Aug. 1993).
Thompson, et al., A System for Anatomical and Functional Mapping of the Human Thalamus, Computers and Biomedical Research, vol. 10, pp. 9-24 (1977).
Trobraugh, J.W., et al., Frameless Stereotactic Ultrasonography: Method and Applications, Computerized Medical Imaging and Graphics, vol. 18, No. 4, pp. 235-246 (1994).
Viant et al., "A Computer Assisted Orthopaedic System for Distal Locking of Intramedullary Nails," Proc. of MediMEC '95, Bristol, 1995, pp. 86-91.
Von Hanwhr et al., Foreword, Computerized Medical Imaging and Graphics, vol. 18, No. 4, pp. 225-228, (Jul.-Aug. 1994).
Wang, M.Y., et al., An Automatic Technique for Finding and Localizing Externally Attached Markers in CT and MR Volume Images of the Head, IEEE Trans. on Biomed. Eng., vol. 43, No. 6, pp. 627-637 (Jun. 1996).
Watanabe et al., "Three-Dimensional Digitizer (Neuronavigator): New Equipment for Computed Tomography-Guided Stereotaxic Surgery," Surgical Neurology, vol. 27, No. 6, Jun. 1987, pp. 543-547.
Watanabe, "Neuronavigator," Igaku-no-Ayumi, vol. 137, No. 6, May 10, 1986, pp. 1-4.
Watanabe, E., M.D., et al., Open Surgery Assisted by the Neuronavigator, a Stereotactic, Articulated, Sensitive Arm, Neurosurgery, vol. 28, No. 6, pp. 792-800 (1991).
Supplementary European Search Report mailed Nov. 2, 2009 for EP02739569 claiming benefit of PCT/US02/17228, filed Jun. 3, 2002, claiming priority from U.S. Appl. No. 09/873,604, filed Jun. 4, 2001 (U.S. Pat. No. 6,636,757, Issued Oct. 21, 2003).
Bucholz, R.D., et al., Intraoperative Ultrasonic Brain Shift Monitor and Analysis, Stealth Station Marketing Brochure. Mar. 1997 (2 pages).
Hamadeh et al, "Kinematic Study of Lumbar Spine Using Functional Radiographies and 3D/2D Registration," TIMC UMR 5525—IMAG. Mar. 19-22, 1997.
Merloz, et al., "Computer Assisted Spine Surgery", Clinical Assisted Spine Surgery, No. 337, (1997) pp. 86-96 (undated).
Weese et al., "An Approach to 2D/3D Registration of a Vertebra in 2D X-ray Fluoroscopies with 3D CT Images," (1991) pp. 119-128.

* cited by examiner

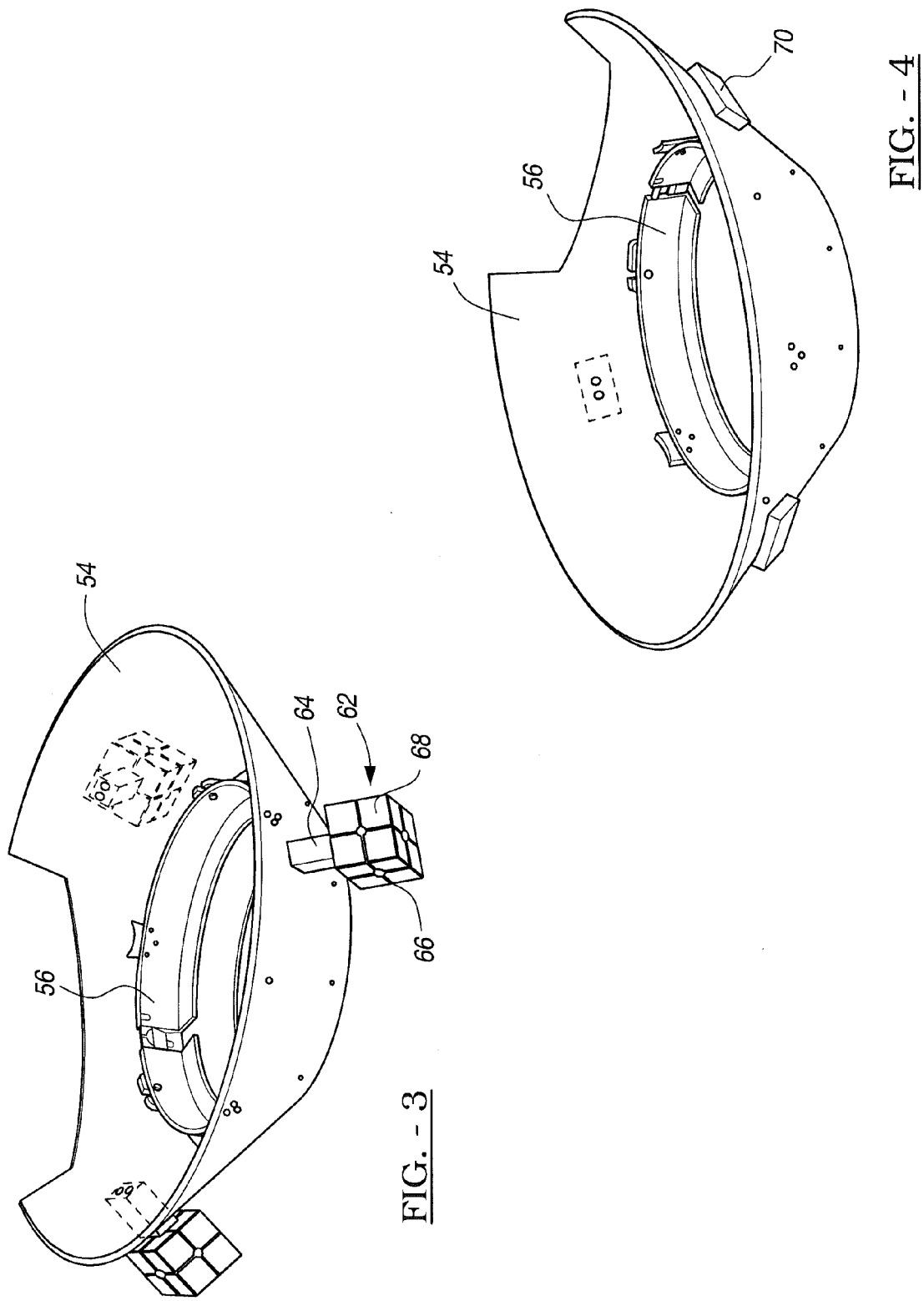

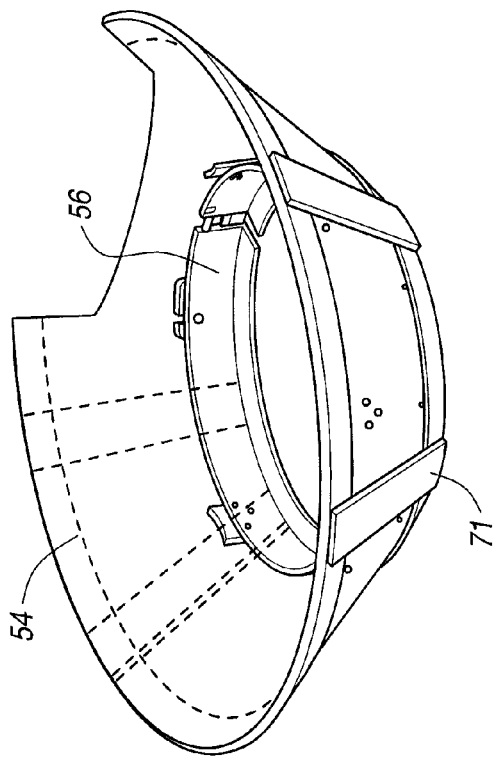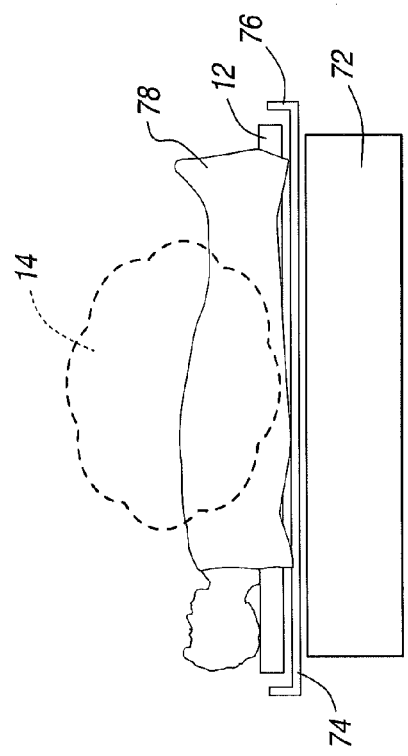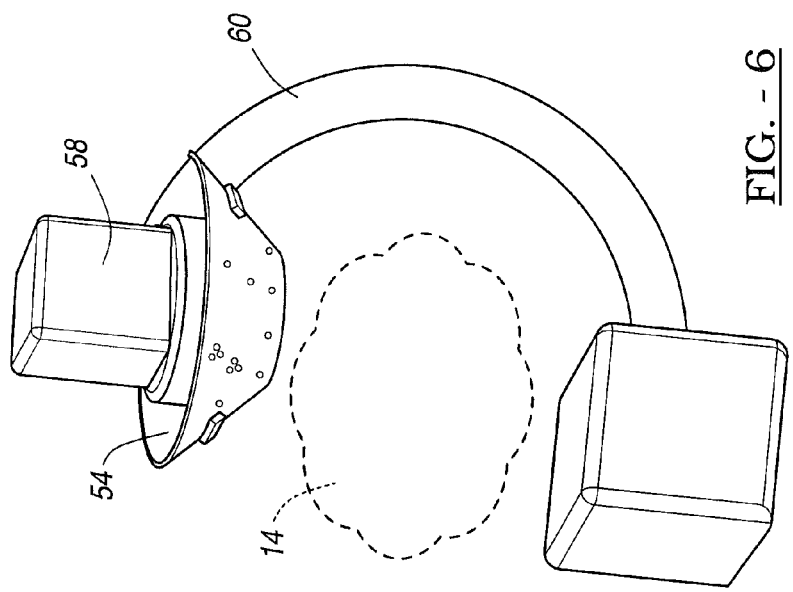

METHOD FOR CALIBRATING A NAVIGATION SYSTEM

CROSS-REFERENCE TO RELATED APPLICATIONS

This application is a divisional of U.S. patent application Ser. No. 10/649,214, filed on Aug. 26, 2003, which is a continuation of U.S. patent application Ser. No. 09/873,604 filed on Jun. 4, 2001, now U.S. Pat. No. 6,636,757, issued on Oct. 21, 2003. The disclosure of the above applications are incorporated herein by reference.

FIELD OF THE INVENTION

This invention relates generally to a method for calibrating a navigation system.

BACKGROUND OF THE INVENTION

Various systems currently exist, which assist in guiding and navigating a surgical probe through a patient undergoing a surgical procedure. These systems include, for example, fluoroscopic, ultrasonic, conductive, optical and electromagnetic type navigation systems.

Various electromagnetic type navigation systems have already been proposed, such as that disclosed in U.S. Pat. No. 4,821,731 to Martinelli, et al., U.S. Pat. No. 5,592,939 to Martinelli and U.S. Pat. No. 5,913,820 to Bladen, et al., which are each hereby incorporated by reference. Advantages of such electromagnetic tracking navigation systems are significant over existing navigation systems. For example, low-frequency electromagnetic waves are not attenuated by the body and therefore, there are no "line-of-sight" issues as with existing optical systems. The transmitter coil array may also be placed underneath or above the patient and the navigated surgical instrument or probe may be used above or below the transmitter coil array. The receiver coils utilized in the surgical instrument or probe are also generally much smaller than existing type navigation systems, which may enable surgical procedures that were previously impossible due to instrument size. The small size of the receiver coils also enable the receiver coils to be placed near the tip of the instrument providing further accuracy and the ability to navigate non-rigid instruments.

However, electromagnetic type navigation systems do have the disadvantage that the electromagnetic field may be distorted by metal objects, sometimes referred to as metallic distortions. In this regard, metal objects that are generally large in size cause the magnetic field to bend, thereby possibly causing inaccuracy in the reported probe position. The other effect of positioning a metal object near the electromagnetic field being navigated is conduction effects. For example, a metal object positioned near or in the electromagnetic field, such as a fluoroscope (C-arm) or an OR table, may create a virtual coil along the metal surface that creates an interference back into the magnetic field. Again, this may create an inaccuracy in the reported probe position because the exact field strengths in the previously known electromagnetic fields have been altered due to the metal object.

In order to reduce or eliminate the effects of distortion due to metal objects, known mathematical models of the electromagnetic fields produced by the transmitter coil array may be utilized. If these mathematical models are accurate, they can be used to represent a set of "known" fields used during the navigation process. However, the disadvantage with using mathematical models for the transmitted fields is that there are inherent inaccuracies in the manufacturing process of the transmitting coils in the transmitting coil array, which can lead to incorrect field values, which are mathematically modeled. These incorrect field values may lead to inaccuracy in the overall navigation process. The mathematical models are also generally very mathematically complex and may, therefore, take an unreasonable amount of time for a computer to calculate and process.

What is needed then is a method and apparatus for electromagnetic navigation of a surgical probe near a metal object, which does not suffer from the above-mentioned disadvantages. This will, in turn, provide electromagnetic navigation of a surgical probe near a metal object that has greater accuracy, provide a shield to reduce or eliminate the effects of the metal object, provide a universal connection to connect the shield to the metal object, provide a calibration process that takes into effect either the shield or the metal object, provide a set of transmitting coils, which may be attached to the shield, integrated into the shield or integrated into the metal object itself, and provide wireless communications in the electromagnetic navigation system for ease of assembly into existing hardware. It is, therefore, an object of the present invention to provide such a method and apparatus for electromagnetic navigation of a surgical probe near a metal object.

SUMMARY OF THE INVENTION

In accordance with the teachings of the present invention, a method and apparatus for electromagnetic navigation of a surgical probe near a metal object is provided.

In one embodiment, an electromagnetic navigation system for use in navigating a probe through an electromagnetic field positioned near a metal object includes a transmitter coil array and a shield. The transmitter coil array has a plurality of transmitter coils and is operable to generate the electromagnetic field to navigate the probe. The shield is positioned adjacent the metal object and is operable to shield the metal object from the electromagnetic field generated by the transmitter coil array, wherein the shield substantially reduces distortion of the electromagnetic field by the metal object.

In another embodiment, an electromagnetic navigation system for use in navigating a probe through an electromagnetic field during a surgical procedure includes a metal instrument and a transmitter coil array. The metal instrument is used during a surgical procedure and is formed at least in part by metallic material. The transmitter coil array has a plurality of transmit coils and is operable to generate the electromagnetic field used to navigate the probe. The transmitter coil array is integrated into the metal instrument, wherein the effects of metallic distortion on the electromagnetic field by the metal instrument is characterized during a calibration process to provide substantially accurate navigation of the probe during the surgical procedure.

In another embodiment, a method for calibrating an electromagnetic navigation system having a transmitter coil array that generates an electromagnetic field is provided. This method includes positioning the electromagnetic navigation system in a working environment to account for metallic distortion caused by a metallic object adjacent to the electromagnetic field, positioning a calibration sensor at a first calibration point, energizing a first coil in the transmitter coil array to generate a first field, sensing the first field strength in the first field with the calibration sensor, and repeating the positioning, energizing and sensing at a second calibration point, wherein effects of metallic distortion caused by the metallic object is taken into account during the calibration process.

Use of the present invention provides a method and apparatus for electromagnetic navigation of a probe through an electromagnetic field near a metal object. As a result, the aforementioned disadvantages associated with the currently available techniques have been substantially reduced or eliminated. Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

Still other advantages of the present invention will become apparent to those skilled in the art after reading the following specification and by reference to the drawings in which:

FIG. 3 is a perspective view of a shield having extended transmitter coils according to the teachings of one embodiment of the present invention;

FIG. 4 is a perspective view of a shield having integrated transmitter coils according to the teachings of another embodiment of the present invention;

FIG. 5 is a perspective view of a shield having integrated transmitter coils according to the teachings of another embodiment of the present invention;

FIG. 6 is a perspective view of a fluoroscope (C-arm) employing the shield of FIG. 4 according to the teachings of the present invention;

FIG. 7 is a side view of an operating room (OR) table having a transmitter coil array (TCA) positioned atop the OR table with a shield positioned between the OR table and transmitter coil array (TCA) according to the teachings of another embodiment of the present invention;

DETAILED DESCRIPTION OF THE PREFERRED EMBODIMENTS

The following description of the preferred embodiments concerning a method and apparatus for electromagnetic navigation of a surgical probe near a metal object is merely exemplary in nature and is not intended to limit the invention or its application or uses. Moreover, while the present invention is described in detail in association with a fluoroscope (C-arm) or an operating room (OR) table, those skilled in the art will readily understand that the present invention may be employed in many other environments having metal objects.

Figure 1:
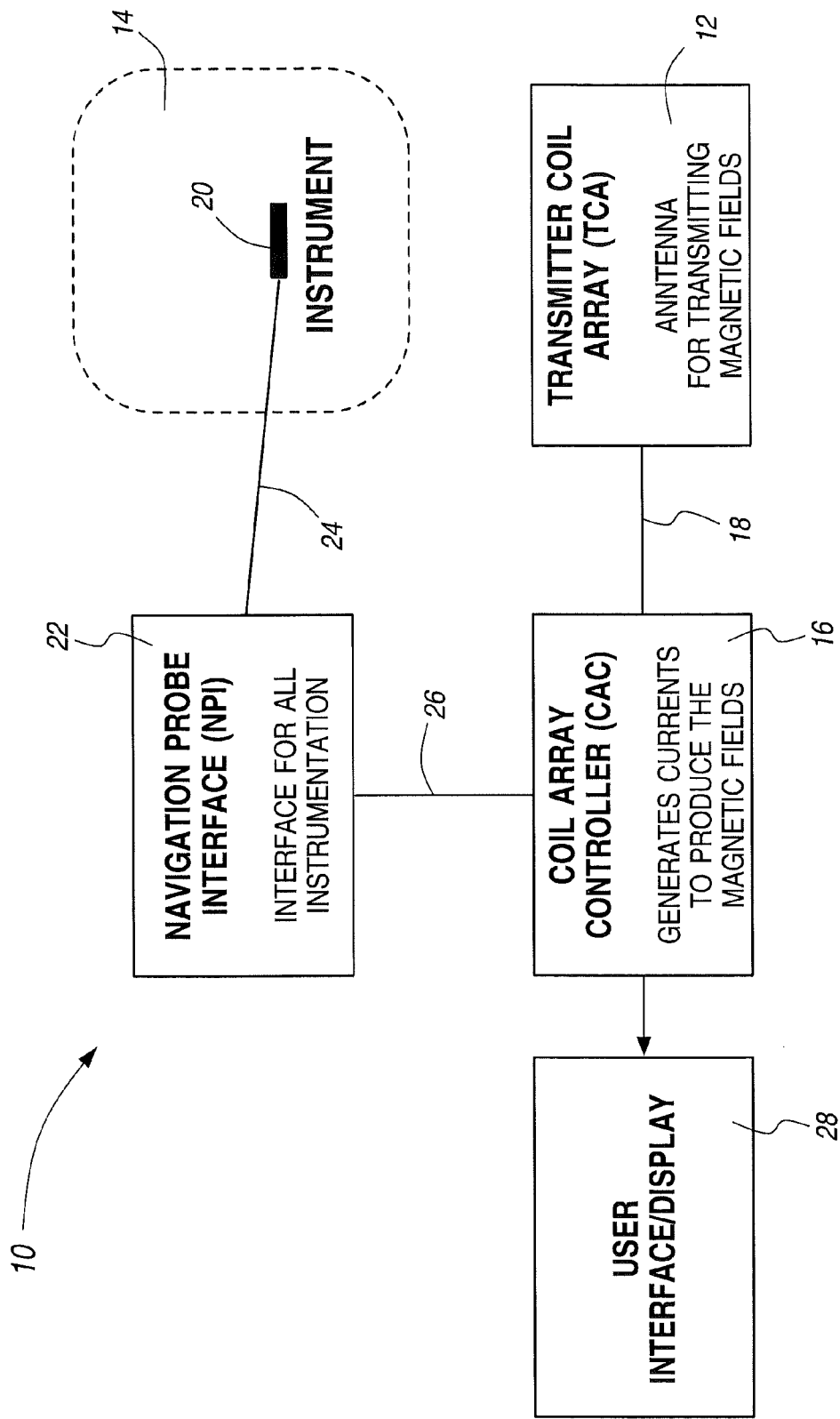
FIG. 1 is an electromagnetic navigation system block diagram according to the teachings of one embodiment of the present invention.

Referring to FIG. 1, an electromagnetic navigation system 10 according to the teachings of one embodiment of the present invention is shown. The electromagnetic navigation system 10 is implemented utilizing a transmitter coil array (TCA) 12, which emits low energy, low frequency AC signals to generate an electromagnetic field or region 14 adjacent to the transmitter coil array 12. The transmitter coil array 12 includes a plurality of coils, further discussed herein, which are driven by a coil array controller (CAC) 16. The coil array controller 16 sources AC current to drive each coil housed within the transmitter coil array 12, via transmission lines 18. The coil array controller 16 may drive the coils housed within the transmitter coil array 12 either sequentially, via time division, or simultaneously, via frequency division, or a combination of both. The electromagnetic field 14 generated by the transmitter coil array 12 provides very accurate known magnetic field strengths over the field of view (FOV) of the electromagnetic navigation system 10. Because the low-frequency electromagnetic waves generated by the transmitter coil array 12 are not attenuated by the body of a patient, there are no line-of-sight issues as with currently available optical systems.

An instrument 20, such as, but not limited to, a surgical probe, catheter, steerable catheter, endoscope, shunt, drill guide, awl/tap, orthopedic implant instrument, etc. located or positioned within the electromagnetic field 14 is able to detect the electromagnetic signal and measure the magnetic field strength by way of small loops of wire or receive coils attached to the instrument 20. The receive coils may be any diameter but are generally made small, for example, about one millimeter to about two millimeters in diameter, which provides for a much smaller instrument 20 than other existing instruments used in navigation systems, such as optically navigated systems. Because of the reduced size of the receiver coils, this enables the receiver coils to be placed near the distal tip of the instrument 20, thereby further reducing accuracy concerns that exist when the receiver coils are positioned more proximally in the instrument 20, since the instrument 20 may bend during navigation. The instrument 20 may include a single receiver coil consisting of multiple loops of wire or a single loop of wire and may also include multiple receiver coils to provide further positional information regarding the instrument 20, as is known in the art and further discussed herein.

The magnetic field strengths sensed by the instrument 20 are received by a navigation probe interface (NPI) 22, via a transmission line 24. The navigation probe interface 22 gathers the magnetic field strengths received by the instrument 20 and processes this information in order to identify the magnetic field strength generated by each coil in the transmitter coil array 12. The navigation probe interface 22 is able to track up to any number of coils, located in the transmitter coil array 12 based on the number of input ports provided, at a sampling rate of about thirty frames per second. The navigation probe interface 22 also directs or triggers the coil array controller 16 to drive each coil located in the transmitter coil array 12 either in a time multiplexed manner, frequency multiplexed manner or a combination of both. The navigation probe interface 22 is generally configured as a digital signal processor (DSP), but may also be configured as discrete logic circuits or any other type of electrical processor. The navigation probe interface 22 is also capable of supporting multiple instruments 20 in a multiplexed manner should this be desirable for the particular surgical procedure.

Once the magnetic field strengths of all the transmitting coils in the transmitter coil array 12 are measured and processed by the navigation probe interface 22, this field strength information is forwarded to the coil array controller 16, via transmission line 26. A general purpose computer or PC incorporated into the coil array controller 16 is then applied to "look-up" the single point in space where the field strengths detected by the receiver coil in the instrument 20 is equivalent to the known field strengths transmitted by the transmitter coil array 12. In this regard, the magnetic field strengths measured by the instrument 20 identify a unique position and orientation in space to determine the X, Y, Z point and the angle and azimuth of the receiver coil located in the instrument 20. Should rotation about the axis of the receiver coil positioned in the instrument 20 be desired, a second receiver coil may be required in the instrument 20. The process used by the coil array controller 16 employs known minimization techniques, such as Newton's method, further discussed herein.

Thus, the electromagnetic navigation system 10 is able to support electromagnetic navigation of the instrument 20 by generating electromagnetic fields from the transmitter coil array 12 throughout the region 14. Instrument 20 measures the magnetic field strengths by way of an electromagnetic sensor or receiver coil. Through design of these electromagnetic fields generated by each coil in the transmitter coil array 12, every position and orientation of each field generated has a unique set of electromagnetic field strengths that is known in the art. These electromagnetic levels or magnetic field strengths generate a system of equations that can be solved mathematically to determine the position and orientation of the instrument 20, as is known in the art.

The localized information which is determined in the coil array controller 16 is then forwarded to an application specific user interface/display 28. The user interface/display 28 may consist of a general purpose computer and a video display to provide image guidance to a surgeon with real time visual feedback of the surgery or navigation being performed. The user interface/display 28 may be configured to provide application specific interfaces for various surgical procedures, such as, but not limited to, cranial, 3-D spine, virtual fluoroscopy, cranial biopsies, tumor resections, craniotomies/craniectomies, thalamotomies/pallidotomies, spinal implant procedures, such as pedicle screw placement, sinus procedures, such as maxillary antrostomies, ethmoidectomies, sphenoidotomies/sphenoid explorations, turbinate resections, and frontal sinusotomies, cardiac mapping procedures, cardiac lead placements, orthopedic, interventional radiology, etc.

Figure 2:
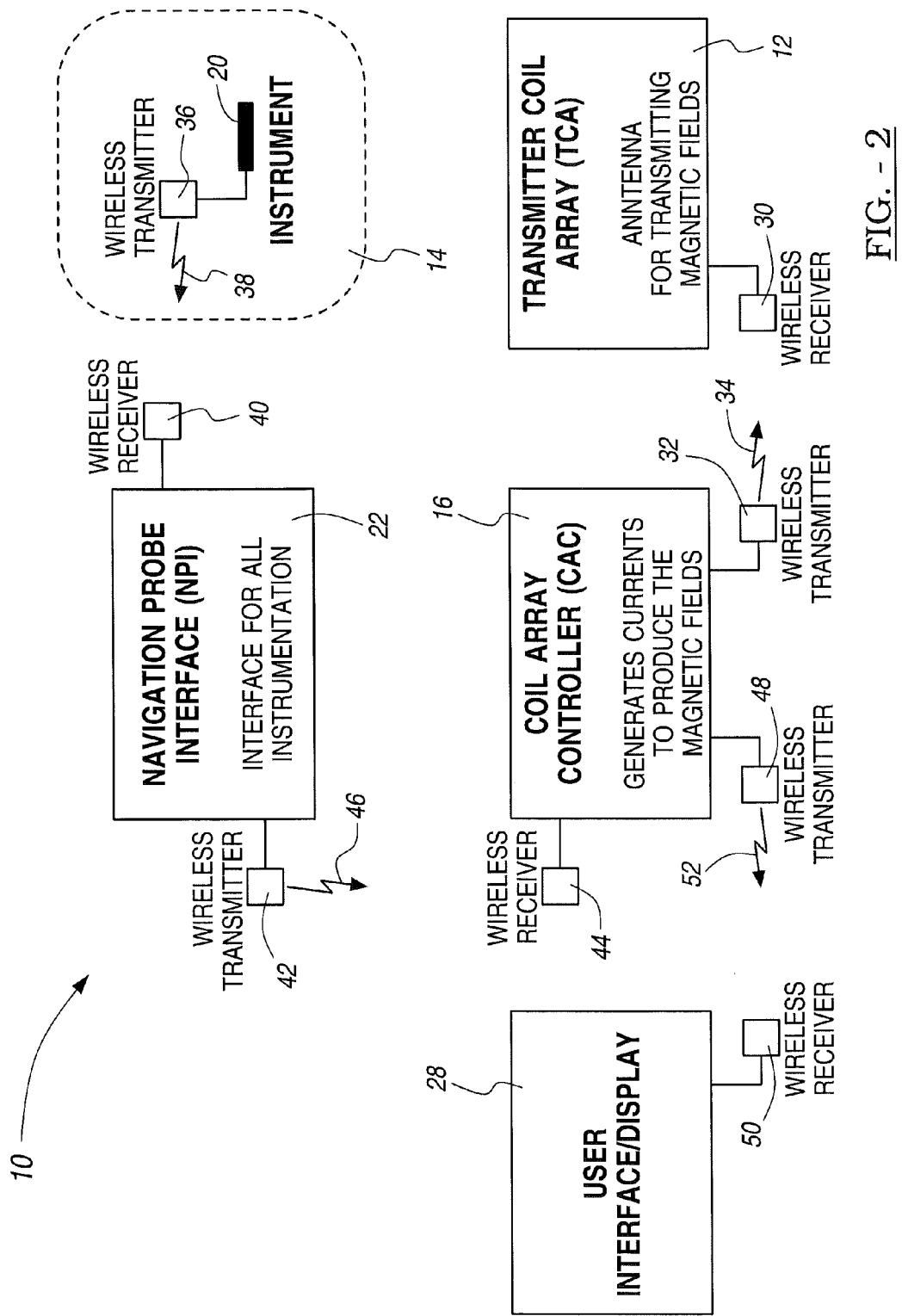
FIG. 2 is an electromagnetic navigation system block diagram according to the teachings of another embodiment of the present invention.

Turning to FIG. 2, the electromagnetic navigation system 10 according to the teachings of another embodiment of the present invention is shown. In this regard, like reference numerals will be used to identify like elements, as set forth in FIG. 1. The electromagnetic navigation system 10 includes the transmitter coil array 12, which is driven by the coil array controller 16 to generate an electromagnetic field or region 14. This electromagnetic field 14 is sensed by the instrument 20 and the navigation probe interface 22 processes the magnetic field strengths sensed by the instrument 20. Again, the navigation probe interface 22 forwards this information to the coil array controller 16, which then determines the position of the instrument 20 in the field or region 14. The location of the instrument 20 is again forwarded to the user interface/display 28 for use by the surgeon during the surgical procedure being performed to provide real time visual feedback of the instrument 20 during the surgical procedure.

The electromagnetic navigation system 10, as shown in FIG. 2, is substantially the same as the electromagnetic navigation system 10, shown in FIG. 1, except that this system employs wireless communications between each element. In this regard, the transmitter coil array 12 includes a wireless receiver 30, which receives control information, via a wireless transmitter 32 coupled to the coil array controller 16. In this configuration, the transmitter coil array 12 will include the amplifiers that are normally positioned in the coil array controller 16 to drive the coils and the coil array controller 16 will simply control the operation of the transmitter coil array 12, via the wireless communication channel 34. Likewise, the instrument 20 includes a wireless transmitter 36 that transmits information over a wireless channel 38 to a wireless receiver 40 in the navigation probe interface 22. The navigation probe interface 22 also includes a wireless transmitter 42, which transmits information to the coil array controller 16, via a wireless receiver 44 over communication channel 46. Finally, the coil array controller 16 forwards navigation information to the user interface/display 28, via a wireless transmitter 48, wireless receiver 50 and wireless channel 52.

The wireless communication or transmission may be accomplished through many types of wireless mediums, such as analog or digital methods. The analog transmission methods may include amplitude modulation (AM), frequency modulation (FM) or phase modulation (PM). Various digital communication standards may also be used such as Ethernet, Blue Tooth or any other type of appropriate digital communication protocol. For example, the wireless communications system, as set forth in Surgical Communications in Power Systems, filed Oct. 28, 1999, U.S. Ser. No. 09/428,722, may be used as one form of wireless communications, which is hereby incorporated by reference. By providing this type of wireless communication of the electromagnetic navigation system 10, as shown in FIG. 2, the transmission lines, as shown in FIG. 1 are substantially eliminated, thereby reducing the amount of cabling required in an operating room environment. This also enables the electromagnetic navigation system 10 to be retrofitted to existing hardware structures without requiring significant modifications to the existing structures. It should further be noted that the electromagnetic navigation system 10 may selectively use both transmission lines and wireless communication.

The electromagnetic navigation system 10 provides significant advantages over existing navigation systems, as discussed above, however, the electromagnetic navigation system 10 must account for electromagnetic navigation near metal objects that may distort the electromagnetic field. This environment typically exists in the operating room and other surgical environments because the metal structure causes or creates distortions in the magnetic field needed for the navigation process. These metal objects, devices or instruments may include, but are not limited to operating room (OR) tables, fluoroscope (C-arms), microscope, ultrasound hand-piece, high-intensity focused ultrasound systems, computer topography imaging (CT), interoperative CT, magnetic resonance imaging (MR), interoperative MR, surgical robot imaging, etc. In order to take into account the distortions caused by such metal objects, the current electromagnetic navigation system 10 may either utilize a shield positioned adjacent to the transmitter coil array 12 to shield the effect of the metal object or the transmitter coil array 12 may be incorporated directly into the metal object and the distortion effect characterized during the calibration process itself since the distortions will generally remain static, further discussed herein.

An exemplary shield 54, shown in FIG. 3, may be used to shield metal objects, such as a fluoroscope (C-arm) (see FIG. 5). The shield 54 is designed to be removably coupled to the C-arm or any other metal object or device requiring shielding by way of a universal band clamp 56. The mounting mechanism or band clamp 56 is able to be adjustably engaged around an intensifier tube 58 of a conventional C-arm 60, which usually has a diameter of about 9 to about 12 inches (see FIG. 5). The shield 54 is substantially conically shaped to substantially reduce or eliminate the effects of the C-arm 60, along with its associated components, such as the intensifier 58. The shield 54 can also be configured in any other shape to create a virtual surface or infinite plane to reflect or shield any type of metal object desired. Reflecting or shielding of these fields prevents field distortion, and thus prevents disturbances by objects on the opposite side of the shield 54.

The shield 54 is formed from a conductive or semi-conductive material, such that the shield's effect on the magnetic field should dominate the effect of the item, such as the C-arm 60 being shielded. The shield 54 may be constructed from materials, such as sheet metal, aluminum, copper, titanium, mu-metal, conductive mylar, etc. The shield 54 may also be formed as a solid shield, a mesh or be modified with holes or slots to reduce the overall weight of the shield 54. Since electromagnetic navigation is generally performed at relatively low frequencies (less than about one megahertz), these frequencies represent long wavelengths that do not pass through the openings, such that the shield 54 essentially acts as a solid shield to these low frequency signals. Therefore, by adding holes or a mesh, the performance of the shield 54 will not be degraded.

Positioned adjacent to or about the periphery of the conically shaped shield 54 is the transmitter coil array 12 which is formed by three sets of transmitting coils 62, which are displaced from the shield 54 by an extension member 64. Each set of transmitting coils 62 consists of three sets of coils 66, each positioned orthogonal to one another and consisting of about fifty wire loops positioned about a cube 68. Offsetting the set of transmitting coils 62 from the shield 54 creates less interference or canceling of the electromagnetic field because of the shield 54 to provide enhanced performance.

Another embodiment of the shield 54 is shown in FIG. 4, where the shield 54 includes three sets of integrally formed transmitting coils 70, also positioned about the perimeter of the shield 54. The transmitting coils 70 are formed substantially adjacent to, or integral with, the shield 54, as opposed to being somewhat displaced from the shield 54, as shown in FIG. 3. While this may create some canceling of the electromagnetic field, this also provides a smaller package should clearance concerns exist in particular applications. The transmitting coils 70 each may include multiple coils configured substantially similar to the set of transmitting coils 62, shown in FIG. 3 or in any other type of configuration. It should further be noted that while the shield 54 shown in FIGS. 3 and 4 include three sets of three orthogonal coils providing for a total of nine coils for navigation purposes, any number of coils or coil configurations may be used. In this regard, generally a minimum of five coils is required to identify the six degrees of freedom (X, Y, Z, angle, azimuth). These coils may be configured with either five transmit coils or more and one receiver coil, or three transmit coils and three receiver coils or any other type of combination. Moreover, should only three degrees of freedom (i.e., X, Y, Z) be desired, only three coils would be required, as is known in the art.

An additional embodiment of the shield 54 is shown in FIG. 5, where the shield includes several integrally formed transmitting coils 71, located about the shield 54. In this regard, the transmitting coils 71 are wrapped and formed integral with the shield 54 with multiple coils extending about the top and bottom perimeter of the shield 54, as well as transmitting coils 71 extending radially from the shield 54. Here again, the coil configuration may be arranged in any manner, as long as each coil has a unique orientation relative to the other coils.

Turning briefly to FIG. 6, the C-arm 60 is shown, which incorporates the shield 54 of the electromagnetic navigation system 10 to generate the electromagnetic field or region 14 for navigating the instrument 20. By using the shield 54, which may be formed integral with the C-arm 60, the distortion created by the C-arm 60 is substantially reduced or attenuated so that accurate navigation of the instrument 20 within the region 14 may be achieved. It should further be noted that either the three sets of transmitting coils 62 or the three sets of transmission coils 70 may be incorporated directly into the C-arm 60. With the three sets of transmitting coils 62 and 70 being an integral part of the C-arm 60, the calibration process may be completed with the entire assembly. If the calibration process is completed in this manner, a separate shield is not required. In this embodiment, the effect of distortion caused by the C-arm 60 or any other metal object on the transmitted fields, would be taken into account and characterized during the calibration process and since these distortions are generally static, accurate navigation is achieved.

Figure 8:
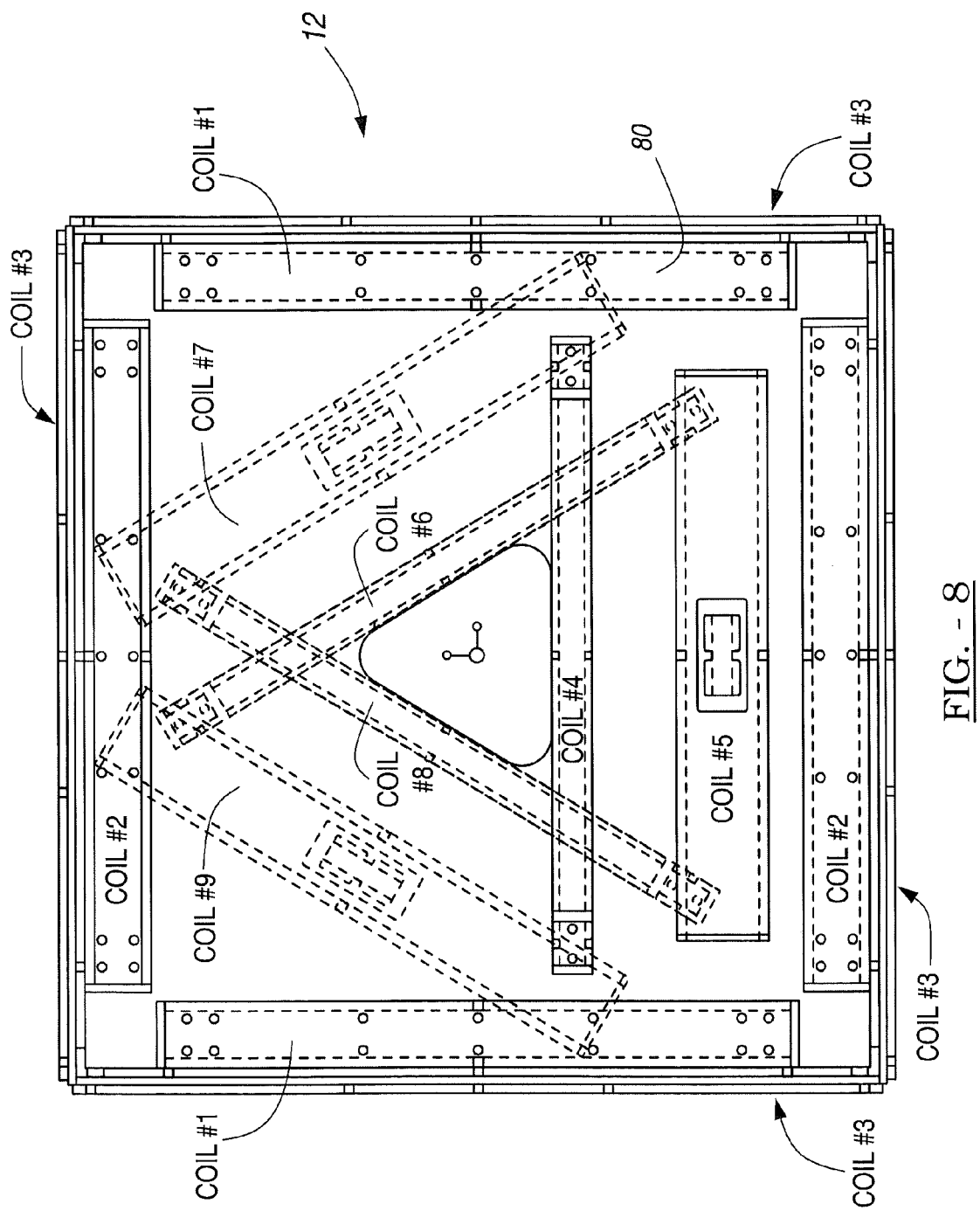
FIG. 8 is a diagram illustrating the transmitter coil array configuration of FIG. 7 in further detail.

Referring to FIGS. 7 and 8, another embodiment of the transmitter coil array 12 is shown incorporated over an operating room (OR) table 72. Positioned between the transmitter coil array 12 and the operating room table 72 is a planar shield 74 having an upturned peripheral lip 76. The shield 74 again acts as an infinite plane to reflect and shield the electromagnetic field or region 14 generated by the transmitter coil array 12 from the metal operating room table 72. The upturned lip 76 also directs the electromagnetic field or region 14 in the vicinity of the patient 78. The OR table 72, shield 74 and transmitter coil array 12 may be separate components or attached to one another.

The configuration of the transmitter coil array 12 used with the OR table is shown in further detail in FIG. 8. The transmitter coil array 12 includes nine discrete coils 80 positioned about the transmitter coil array 12. Each coil 80 is located or positioned at a different orientation relative to the remaining coils 80, such that each coil 80 generates its own unique electromagnetic field. Three sets of coils 80 are generally driven at a time so that there are three sets of three coils 80 driven sequentially with each coil 80 in each set of three driven at its own unique frequency to identify that particular field. Here again, other types of coil arrangements and numbers of coils may be utilized in the electromagnetic navigation system 10. Moreover, as shown herein, the transmitter coil array 12 may be configured in any number of ways to accommodate for its particular application and the use in association with the C-arm 60 and the OR table 72 are merely exemplary in nature.

Figure 9:
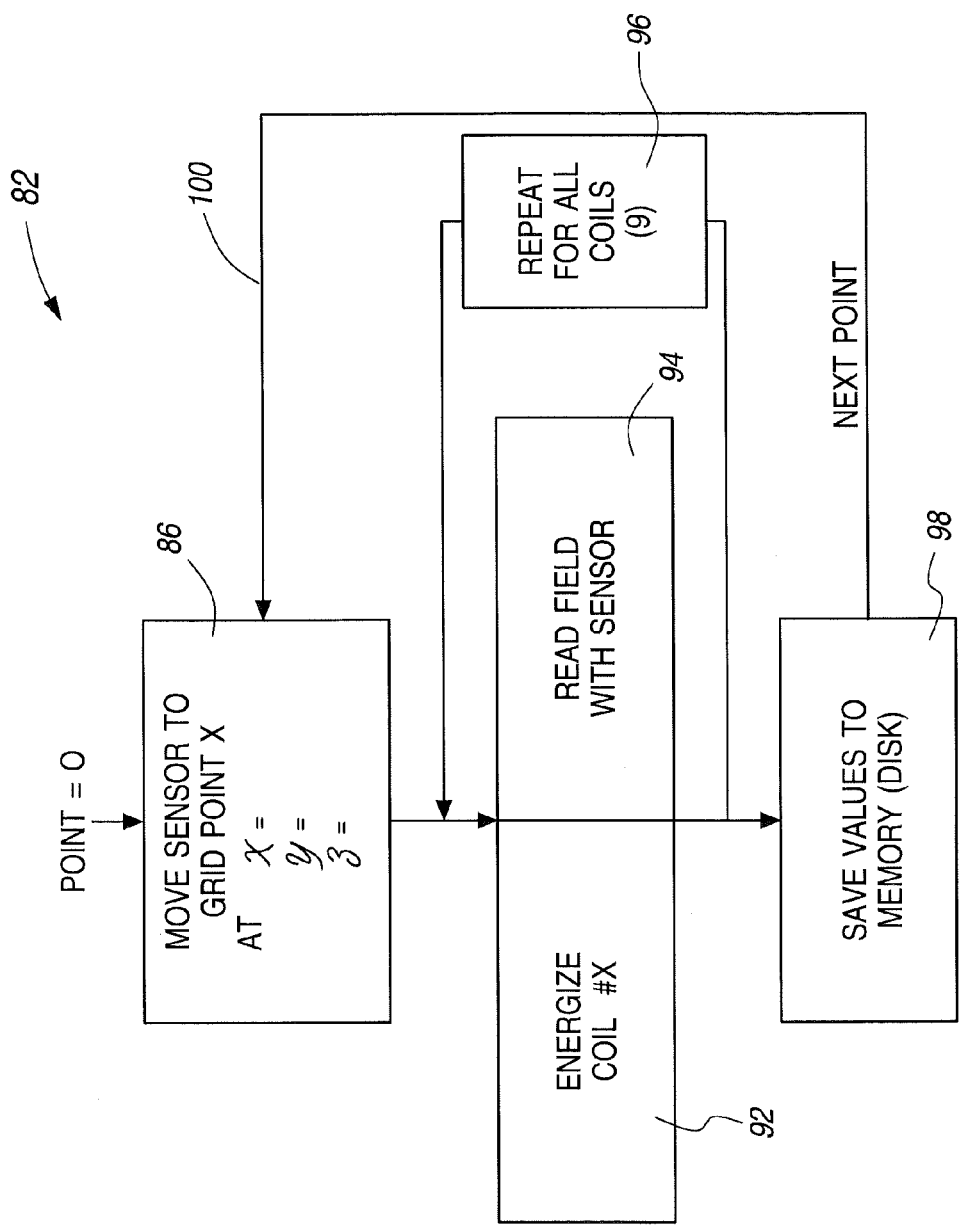
FIG. 9 is an illustration of a calibration process according to the teachings of the present invention.
Figure 10:
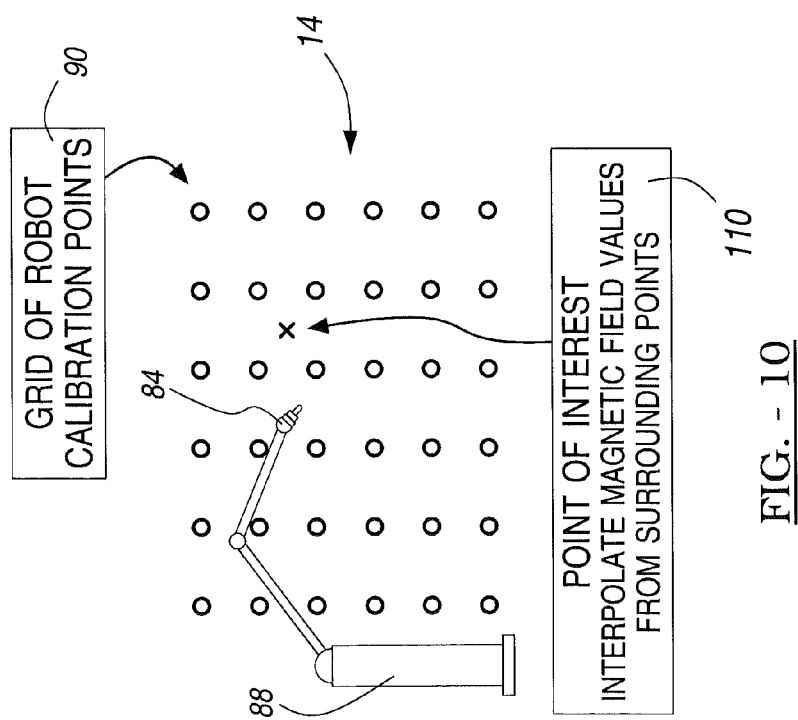
FIG. 10 is a two dimensional grid of robotically measured calibration points used in the calibration process according to the teachings of the present invention.

Turning now to FIGS. 9 and 10, the calibration process 82 according to the teachings of the present invention is disclosed in further detail. The calibration process 82 is conducted at the factory and is implemented by simulating the environment in which the electromagnetic navigation system 10 will be employed. In this regard, should a shield 56 or 74 be used, as is shown in FIGS. 6 and 7, that particular configuration with the C-arm 60 or the OR table 72 will be calibrated at the factory prior to shipment of the electromagnetic navigation system 10 to characterize the effects of the particular metal object or surgical device being used. Likewise, should the transmitter coil array 12 be integrally formed or incorporated directly into the surgical device having metallic portions rather than retrofitting the surgical device with the shield, the surgical device with the incorporated electromagnetic navigation system 10 will also be calibrated prior to shipment or delivery. This calibration process 82 assumes that the distortion from the metal object or device will remain static.

The calibration process 82 starts by moving a calibration sensor 84 to a point in the electromagnetic field or region 14 at step 86. Preferably, the starting point will be identified as the origin (i.e., equals zero) and all other measured points will be referenced back to this origin. In this regard, a robotic calibration arm or unit 88 having the calibration sensor 84 (see FIG. 10) is employed to measure the magnetic field strength of each energized coil, along a pre-determined grid of calibration points 90. As shown in FIG. 10, a two-dimensional grid is illustrated having a plurality of calibration grid points 90 disposed equally throughout the two-dimensional grid. For example, each grid point 90 may be separated every 15 millimeters. During the calibration process 82, a three-dimensional grid will be employed to measure the magnetic field strength of each calibration point 90 throughout the region 14 for each coil in the transmitter coil array 12. For example, a one meter cubed ($m^3$) region 14 may be separated into several calibration grid points 90, such as eight thousand grid points 90, which are sensed by the calibration sensor 84 on the robotic unit 88 as the calibration sensor 84 is positioned at each one of these discrete grid points 90.

Referring back to FIG. 9, with the calibration sensor 84 positioned at the first grid point 90 or origin at step 86, one of the coils in the transmitter coil array 12 is energized at step 92 and the magnetic field strength generated is sensed or read at this grid point 90 with the calibration sensor 84 at step 94. Again, the navigation probe interface 22 instructs the coil array controller 16 to drive a particular coil in the transmitter coil array 12. With the magnetic field sensed by the calibration sensor 84, the magnetic field strength is determined for that particular calibration point 90 by the navigation probe interface 22. Each coil in the transmitter coil array 12 is then driven by the coil array controller 16 at that particular calibration point 90, via step 96. With the magnetic field strength values known for each coil in the transmitter coil array 12, these magnetic field strengths are then stored to memory at step 98. In this regard, these magnetic field strengths are forwarded from the navigation probe interface 22 through the general purpose computer in the control array controller 16 and stored on a flash ROM or any other type of memory housed within the transmitter coil array 12. In this way, the transmitter coil array 12 may be operated by any coil array controller 16, since the calibration values are stored with the transmitter coil array 12.

The calibration process 82 continues by moving to a next calibration point 90 at step 100 to again determine the magnetic field strengths from each coil. With the navigation probe interface 22 synchronizing the coil array controller 16 to drive each coil in the transmitter coil array 12 and with the robotic unit 88 positioning the calibration sensor 84 at each calibration point 90 within the three-dimensional calibration grid, the calibration process 82 continues until all of the field strengths for all of the coils at each calibration point 90 in the calibration grid is stored. Accordingly, the calibration process 82 stores actual measurements of the magnetic field strength generated by the transmitter coil array 12, while taking into account or characterizing the distortion effects of either the particular shield, coupled to the surgical device or the transmitter coil array 12 incorporated directly into the surgical device. In this way, any metallic distortions caused by the metal object or device, such as the C-arm 60 or the OR table 74 is taken into account by performing the real time measurements with these objects in place. Therefore, any distortions caused by utilizing the electromagnetic navigation system 10 in its environment are already accounted for during the factory calibration process to provide accurate navigation of the instrument.

Figure 12:
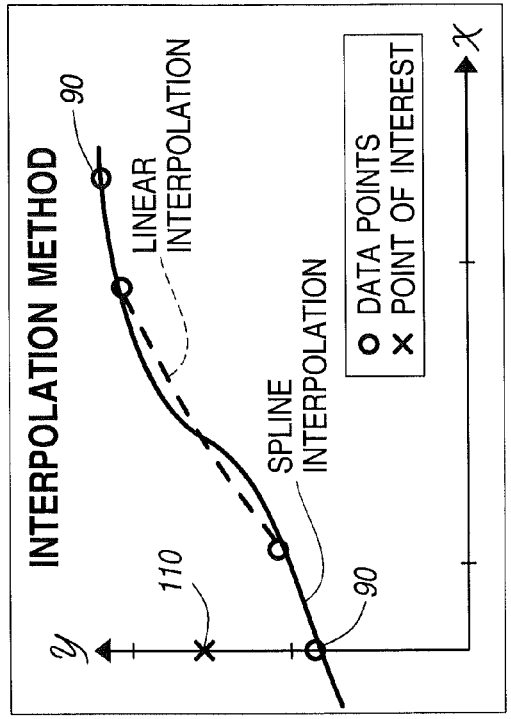
FIG. 12 is a graph illustrating two interpolation methods utilized in the navigation process according to the teachings of the present invention.
Figure 11:
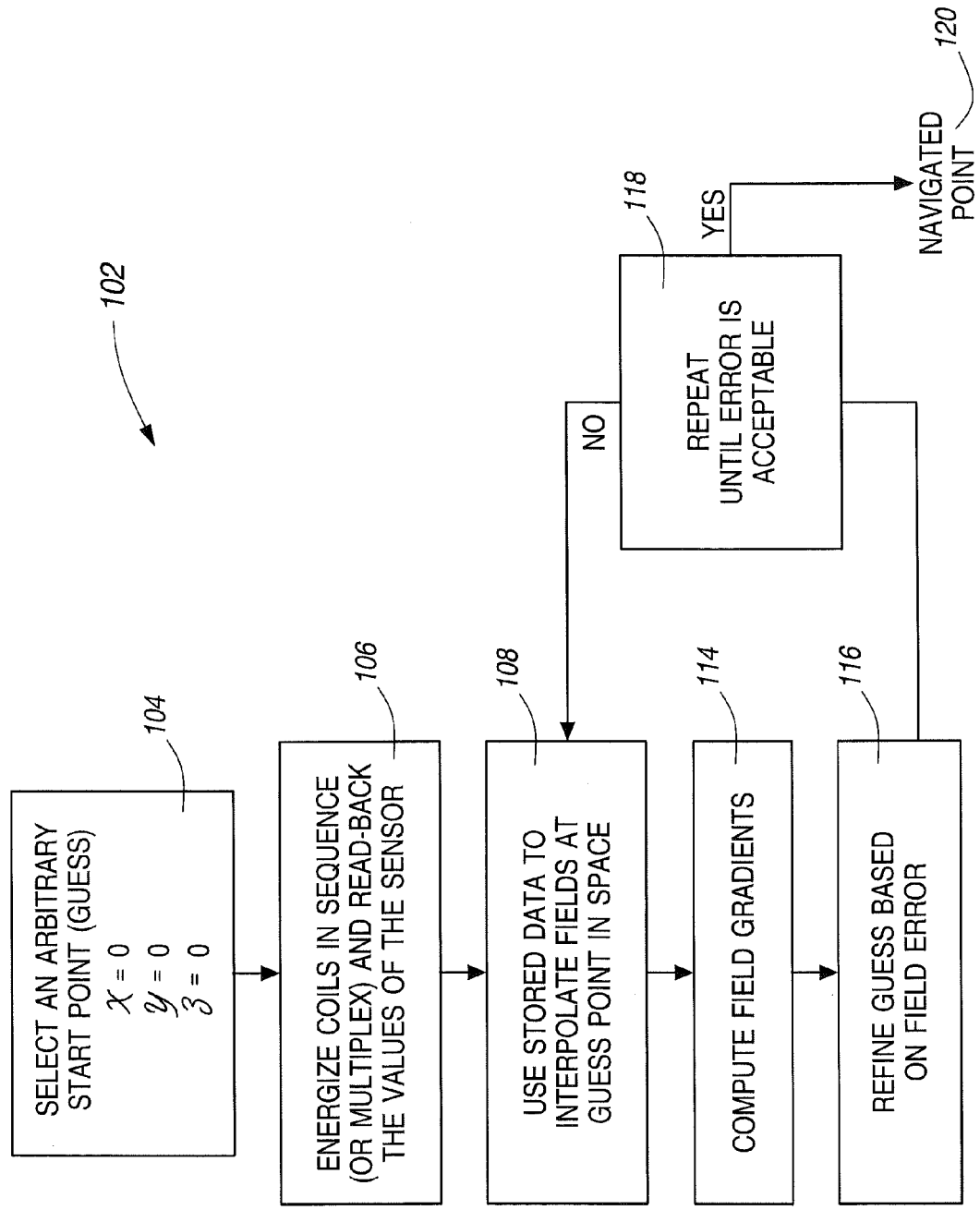
FIG. 11 is an illustration of a navigation process according to the teachings of the present invention.

Referring now to FIGS. 10-12, the navigation process 102 will be described in further detail. The navigation process 102 is a minimization process, as is known in the art, such as Newton's method, which begins at step 104. At step 104, an arbitrary starting point is selected, which is generally the center of volume of the region 14 (i.e., 0, 0, 0). Once the arbitrary start point or guess point 110 is selected at step 104, the navigation process 102 continues to step 106 where the coils in the transmitter coil array 12 are energized, either sequentially or by frequency multiplexing and the magnetic field strength values are received by the sensor located in the instrument 20. Once these values are determined at step 106, the navigation process continues to step 108 where the previously stored calibration data or field strengths for the calibration points 90 in the calibration grid are used to interpolate the fields at the guess point 110 in space. In this regard, should the guess point 110 not be one of the known calibration grid points 90, the guess point 110 is interpolated using known interpolation techniques. These techniques, for example, may include linear interpolation or spline interpolation as shown in FIG. 12. The location of the guess point 110 may be determined from the known calibration grid points 90 using these known interpolation methods to determine the magnetic field strengths between the known calibration grid points 90. Additionally, any other type of interpolation method may also be used such as polynomial curve fitting, etc.

Once the field strengths are determined for the guess point 110 at step 108, the navigation process 102 continues to step 114 where computation of the field gradients or the difference in field strengths between the guess point 110 and the measured fields at the instrument location are determined. These field gradients or errors are then used at step 116 to refine the guess point 110 during the minimization process to select a new guess point 110 which is closer to the actual sensor location. Once the refined guess point 110 is determined, this process is continued without requiring additional measurements from the instrument 20 until the error between the guess point 110 and the actual instrument location is minimized to an acceptable value at step 118. If the error value is not acceptable, the navigation process 102 again continues with a new guess point 110 selected which is closer to the actual instrument location and the error again computed, via the steps in blocks 108, 114 and 116. Should the error be acceptable, as determined in step 118, the navigation process 102 ends with the guess point 110 now representing the actual instrument location or navigated point 120. In this way, navigation of the instrument 20 is performed very accurately without having metal objects effect the overall navigation since the calibration process has already taken into effect the metal object during creation of the look-up table for the calibration grid points 90, which is used during the navigation process 102.

Figure 13:
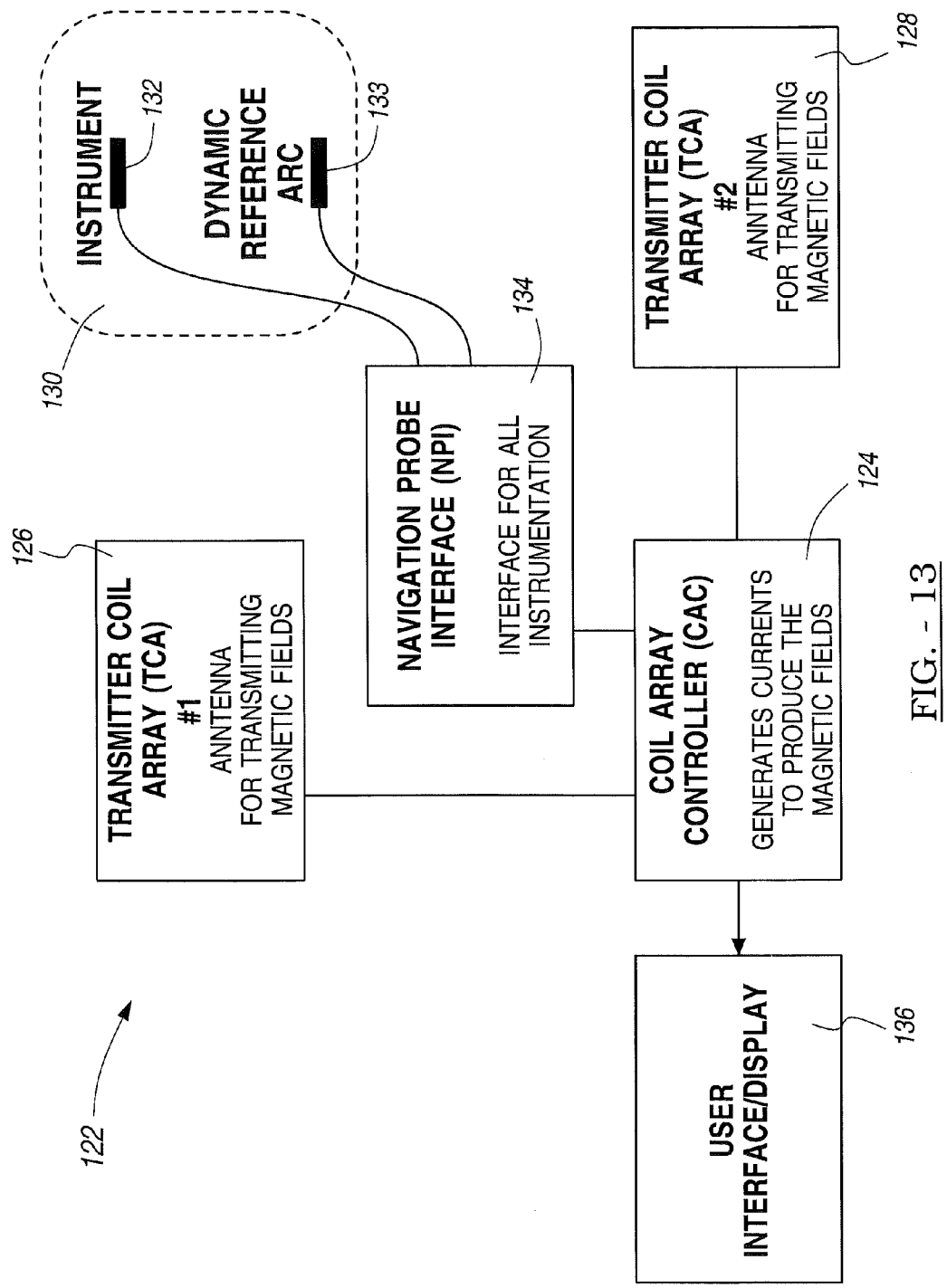
FIG. 13 is an electromagnetic navigation system block diagram according to the teachings of another embodiment of the present invention.
Figure 14:
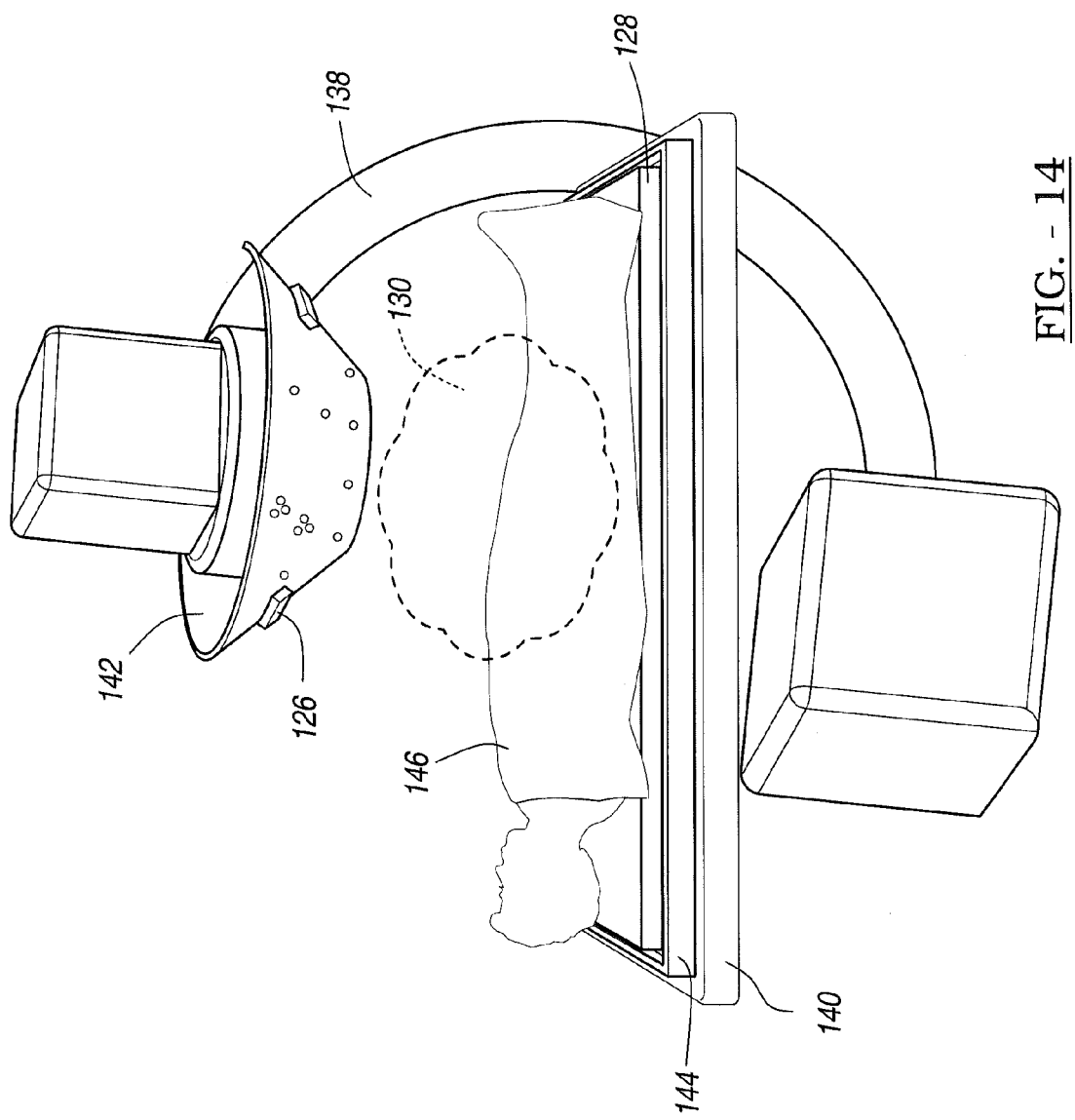
FIG. 14 illustrates the electromagnetic navigation system of FIG. 13 associated with a fluoroscope (C-arm) and an OR table.

Finally, referring to FIGS. 13 and 14, an electromagnetic navigation system 122 according to the teachings of another embodiment of the present invention is shown. The electromagnetic navigation system 122 is substantially similar to the electromagnetic navigation systems 10, shown in FIGS. 1 and 2, except that the electromagnetic navigation system 122 includes an additional transmitter coil array and a dynamic reference arc. In this regard, the electromagnetic navigation system 122 includes a coil array controller 124 which drives a first transmitter coil array 126, as well as a second transmitter coil array 128. Both transmitter coil arrays 126 and 128 generate an electromagnetic field or region 130 where the instrument 132 is navigated and a dynamic reference arc 133 is positioned. Here again, instrument 132 provides the received magnetic field strengths to navigation probe interface 134 for processing and forwarding to the coil array controller 124 and the dynamic reference arc 133 is used for a reference by the instrument 132, further discussed herein. The coil array controller 124 again forwards the navigation information to a user interface/display 136 for use during the surgical procedure being performed.

The electromagnetic navigation system 122 is shown configured in FIG. 14 in association with a C-arm 138 and an OR table 140. Here again, the transmitter coil array 126 may be configured within shield 142 of the C-arm 138 or incorporated directly into the C-arm 138. The transmitter coil array 128 is shown positioned above the OR table 140 with a shield 144 positioned therebetween.

By providing both the transmitter coil array 126 and the transmitter coil array 128 to generate the electromagnetic field or region 130 about the patient 146, each transmitter coil array 126 and 128 may be driven simultaneously, sequentially or independent from one another. In this regard, the coil array controller 124 is capable of driving the transmitter coil arrays 126 and 128 simultaneously at different frequencies so that the particular fields may be identified. Alternatively, the transmitter coil arrays 126 and 128 may be time multiplexed or driven sequentially, via the coil array controller 124 . In other situations, it may be desirable to initially drive the transmitter coil array 126 located on the C-arm 138 during the surgical procedure while the C-arm 38 generates a fluoroscopic image. However, the C-arm 138 may be in the way for certain portions of the surgical procedure. If so, the C-arm 138 may be rotated or moved our of the way after the image is captured to provide for further surgical clearance while still conducting navigation, via the second transmitter coil array 128 associated with the OR table 140.

In this way, navigation handoff can be performed between both transmitter coil arrays 126 and 128 without requiring the surgeon to have to stop during the overall surgical procedure should one of the particular metal or surgical instruments be in the way. The dynamic reference arc 133 is substantially similar to the instrument 132 in that it includes receive coils capable of providing six degrees of freedom information. However, the dynamic reference arc 133 is used as a reference and is fixed relative to the patient being navigated to provide a reference point for the instrument 132. In other words, the instrument 132 may be referenced back to either transmitter coil array 126 or 128 and the dynamic reference arc 133 may be also referenced back to the transmitter coil arrays 126 and 128 to determine the relative positions of each. By having this information, the instrument 132 may then be simply referenced back to the dynamic reference arc 133 by simple subtraction of the fields, as is known in the art, which removes the transmitter coil arrays 126 and 128 out of the calculation process, thereby enabling unobstructed hand-offs between the transmitter coil array 126 and the transmitter coil array 128. Use of the dynamic reference arc 133 may also be employed with the navigation system 10, shown in FIGS. 1 and 2 should this be desired. An example of such hand off technology is set forth in System For Translation of Electromagnetic and Optical Localization Systems, filed Oct. 28, 1999, U.S. Ser. No. 09/429,568, which is hereby incorporated by reference. Moreover, it should be further noted that the calibration process 82 will be performed with both the C-arm 138 and the OR table 140 in proximity to one another, as shown in FIG. 14 to take into effect the entire surgical environment, thereby providing further accuracy and surgical versatility.

The electromagnetic navigation systems 10 and 122, therefore, provide for very accurate surgical navigation of the instruments 20 and 132 during the surgical procedure because the calibration process 82 takes into account and characterizes the distortion effect of the surgical device used during the surgical procedure. This accuracy is achieved by using the information determined during the calibration process 82 in the navigation process 102. In this way, accurate navigation of the instruments 20 and 132 are achieved in an efficient, cost effective and versatile manner that also takes into effect the tolerance of the transmitter coil array and the surrounding environment.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for calibrating an electromagnetic navigation system having a transmitter coil array that generates an electromagnetic field in a procedure region, said method comprising:
 (a) positioning the electromagnetic navigation system in a working environment having a metallic object outside of the procedure region of the electromagnetic field that causes a metallic distortion in the electromagnetic field in the procedure region, wherein an instrument is positionable in the procedure region within a portion of the electromagnetic field;
 (b) positioning a calibration sensor at a first calibration point in the procedure region of the working environment;
 (c) energizing a first coil in the transmitter coil array to generate a first field of the electromagnetic field;
 (d) sensing a first field strength of the first field with the calibration sensor in the procedure region; and
 (e) positing the calibration sensor at a second calibration point in the procedure region of the working environment and repeating (c) and (d) at the second calibration point, wherein effects of the metallic distortion caused by the metallic object are taken into account during the calibration and wherein the metallic object is a medical device.

2. The method as defined in claim 1 wherein positioning the calibration sensor at a first calibration point further comprises utilizing a robotic unit to position the calibration sensor at the first calibration point.

3. The method as defined in claim 1 further comprising creating a look-up table for a plurality of calibration points which is operable to be used during a navigation process, where the look-up table stores field strengths for the plurality of calibration points that take into affect the metallic distortion of the electromagnetic field caused by the metallic object.

4. The method as defined in claim 1 further comprising energizing the plurality of coils in the transmitter coil array in at least one of a time division multiplex manner, frequency division multiplex manner, or a combination of both.

5. The method as defined in claim 1 further comprising energizing a plurality of coils sequentially in the transmitter coil array to generate a plurality of fields of the electromagnetic field and sensing field strengths of each of the plurality of fields with the calibration sensor.

6. The method as defined in claim 5 further comprising repeating step (e) to generate about eight thousand calibration points.

7. The method as defined in claim 5 wherein the medical device is selected from a group consisting of an operating room table, fluoroscope, a microscope, an ultrasound hand piece, a high-intensity focused ultrasound systems, a computer topography imaging (CT)system, an interoperative computer topography, system, a magnetic resonance imaging (MR) system, an interoperative magnetic resonance system and a surgical robot.

8. The method as defined in claim 7 wherein at least one of function and movement of the medical device is simulated during the calibration process.

9. The method of claim 8, further comprising:
determining an orientation and location of a metal object.

10. The method of claim 9, wherein determining an orientation and location includes;
predetermining a position of the metal object in an area where the electromagnetic navigation system is to be used; and
maintaining the orientation and location of the metal object in the area.

11. The method as defined in claim 1 further comprising:
storing the sensed first field strength at the first calibration point and the second calibration point in a memory device; and
navigating a probe through the electromagnetic field by using the stored field strengths sensed by the calibration sensor.

12. The method as defined in claim 11 wherein navigating the probe includes navigating a probe selected from at least one of a surgical probe, catheter, steerable catheter, endoscope, shunt, drill guide, awl/tap, orthopedic instrument and a combination thereof.

13. The method as defined in claim 11 further comprising providing a dynamic reference arc that is affixed relative to a patient and used as a reference point for the probe.

14. The method as defined in claim 11 further comprising comparing the stored field strengths sensed by the calibration sensor with field strengths measured by the probe.

15. The method as defined in claim 14 further comprising using the stored field strengths sensed by the calibration sensor to interpolate fields at a guess point in space.

16. The method as defined in claim 15 further comprising computing the difference in field strengths between the guess point with the field strength measured by the probe.

17. The method as defined in claim 16 further comprising using the measured difference to refine the guess point during a minimization process to select a new guess point that is closer to the probe location.

18. The method as defined in claim 17 further comprising minimizing the error between the guess point and the actual location of the probe to an acceptable value.

19. The method of claim 18, further comprising:
selecting the guess point in three dimensional space; and
determining the error between electromagnetic field strengths at the selected guess point and the sensed electromagnetic field strengths at the actual location of the probe; and
wherein the actual location of the probe is the location of the probe in three dimensional space.

20. A method for calibrating an electromagnetic navigation system having a transmitter coil array that generates an electromagnetic field in a three dimensional space, said method comprising:
positioning a metallic object adjacent at least a procedure region of the electromagnetic field;
positioning a calibration sensor at a first calibration point in the three dimensional space, energizing a plurality of coils sequentially in the transmitter coil array to generate a plurality of fields of the electromagnetic field;
sensing first field strengths of each of the plurality of fields with the calibration sensor at the first calibration point; and
moving the calibration sensor to a second calibration point in the three dimensional space different from the first calibration point, energizing the plurality of coils sequentially in the transmitter coil array to generate the plurality of fields;
sensing second field strengths of each of the plurality of fields with the calibration sensor at the second calibration point; and
storing the sensed first field strengths and the second field strengths;
wherein effects of metallic distortion caused by the metallic object is taken into account during the calibrating at least by sensing the generated first field strengths and second field strengths that include distortion due to the metallic object.

21. The method of claim 20, further comprising:
maintaining the position of the metallic object relative to the transmitter coil array after calibrating the electromagnetic system having the transmitter coil array.

22. The method as defined in claim 20 further comprising positioning the calibration sensor at a plurality of different calibration points in the three dimensional space different from any previous calibration point, energizing the plurality of coils sequentially in the transmitter coil array to generate the plurality of fields, and sensing a field strength of each of the plurality of fields with the calibration sensor at each of the plurality of different calibration points;
wherein the metallic object is away from the plurality of different calibration points and affects the sensed field strength at each calibration point.

23. The method of claim 22, wherein positioning the calibration sensor at a plurality of different calibration points in the three dimensional space includes moving the calibration sensor to each of the plurality of different calibration points with a robotic unit.

24. The method of claim 22, wherein the plurality of different calibration points is in a grid pattern in the three dimensional space.

25. The method of claim 22, wherein the plurality of different calibration points include substantially all of the points that are about 15 millimeters apart in a one (1) cubic meter three dimensional volume.

26. The method of claim 25, wherein the sensed field strengths at all of the plurality of different calibration points in the three dimensional volume are stored in a storage device.

27. The method of claim 26, wherein the storage device stores all of the sensed field strengths at the plurality of different calibration points in a look-up table that is operable to be accessed during a navigated procedure.

28. The method of claim 27, further comprising:
interpolating a physical location of an instrument in the three dimensional space based upon the stored plurality of different calibration points including:
positioning an instrument in the three dimensional space at an instrument point;
energizing the plurality of coils in the transmitter coil array to generate fields;
sensing field strengths of the fields generated by the plurality of coils in the transmitter coil array at the instrument point; and
comparing the sensed fields at the instrument point to the look-up table.

29. The method of claim 28, further comprising:
interpolating a sensed field strength relative to those in the look-up table when the sensed field at the instrument is not identical to one of the sensed field strengths at the plurality of different calibration points in the look-up table.

30. The method of claim 29, wherein interpolating the sensed field strength includes linear interpolation and spline interpolation of the sensed field strength relative to those in the look-up table.

31. The method of claim 29, wherein comparing the sensed fields at the instrument to the look-up table includes:
selecting a guess point in the three dimensional space;
determining an error between field strengths at the selected guess point and the sensed fields at the instrument point; and
minimizing the determined error.

32. A method for calibrating an electromagnetic navigation system having a transmitter coil array integral with a metallic object that generates an electromagnetic field in a three dimensional space, said method comprising:
operating the transmitter coil array that is integral with the metallic object that generates the electromagnetic field in the three dimensional space;
positioning a calibration sensor at a calibration position in three dimensional space;
instructing a coil array controller to drive a particular coil in the transmitter coil array to generate at least a portion of the electromagnetic field that includes metallic distortion effect due to the metallic object;
sensing at least a portion of the electromagnetic field having the metallic distortion effect with the calibration sensor at the calibration position;
determining an electromagnetic field strength of the sensed at least a portion of the electromagnetic field having the metallic distortion effect for the calibration position by a navigation probe interface; and
storing the determined electromagnetic field strength at the calibration position with a storage device;
wherein effects of metallic distortion effect caused by the metallic object is taken into account during the calibrating at least by sensing the generated at least a portion of the electromagnetic field that includes distortion due to the metallic object.

33. The method of claim 31, wherein positioning a calibration sensor at a calibration position in three dimensional space includes positioning the calibration sensor at a plurality of different positions in the three dimensional space and sensing electromagnetic field strengths generated by a plurality of coils of the transmitter coil array.

34. The method of claim 33, wherein instructing a coil array controller to drive a particular coil in the transmitter coil array includes driving the particular coil in a time multiplex manner, frequency multiplex manner, or sequential manner relative to other coils in the transmitter coil array.

35. The method of claim 33, wherein the plurality of different positions in the three dimensional space substantially defines a selected grid of points in the three dimensional space;
wherein positioning a calibration sensor at the plurality of different positions in the three dimensional space includes moving the calibration sensor with a robotic device to each point of the selected grid of points in the three dimensional space.

36. The method of claim 33, further comprising:
maintaining the position of the metallic object relative to the transmitter coil array after storing the determined electromagnetic field strengths at the plurality of different positions.

37. The method of claim 32, wherein the determined electromagnetic field strengths generated by all of the coils of the transmitter coil array are stored in the storage device.

38. The method of claim 37, wherein all of the stored determined electromagnetic field strengths are saved in a look-up table.

39. The method of claim 38, further comprising:
determining a location of an instrument in the three dimensional space including:
sensing a generated electromagnetic field strength of all of the coils in the transmitter coil array in three dimensional space;
comparing the sensed electromagnetic field strengths generated by all of the coils in the transmitter coil array to the look-up table; and
determining the location of the instrument based upon the comparison of the sensed electromagnetic field strengths with the instrument to the look-up table.

40. The method of claim 39, wherein comparing the sensed electromagnetic field strengths generated by all of the coils in the transmitter coil array to the look-up table includes:
selecting a guess point in three dimensional space;
determining an error between electromagnetic field strengths at the selected guess point and the sensed electromagnetic field strengths at the instrument point; and
minimizing the determined error.

41. The method of claim 36, further comprising:
interpolating between stored electromagnetic field strengths to determine the location of the instrument in the three dimensional space if the sensed electromagnetic field strengths with the instrument are not identical to stored strengths in the storage device.

42. The method of claim 41 wherein the plurality of different positions in the three dimensional space defines a grid in the three dimensional space to allow for interpolation between the plurality of different positions in the three dimensional space.

43. The method of claim 42, wherein the grid in the three dimensional space is defined by the plurality of different positions about 15 millimeters apart within the three dimensional space.

44. The method of claim 43, wherein the three dimensional space is about one (1) cubic meter.

\* \* \* \* \*